United States Patent
Keusenkothen et al.

(10) Patent No.: US 9,315,430 B2
(45) Date of Patent: Apr. 19, 2016

(54) REACTOR COMPONENTS

(71) Applicants: Paul F. Keusenkothen, Houston, TX (US); Frank Hershkowitz, Basking Ridge, NJ (US); Gary D. Mohr, Houston, TX (US); ChangMin Chun, Annandale, NJ (US); Jeffrey W. Frederick, Centreville, VA (US)

(72) Inventors: Paul F. Keusenkothen, Houston, TX (US); Frank Hershkowitz, Basking Ridge, NJ (US); Gary D. Mohr, Houston, TX (US); ChangMin Chun, Annandale, NJ (US); Jeffrey W. Frederick, Centreville, VA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 230 days.

(21) Appl. No.: 13/658,851

(22) Filed: Oct. 24, 2012

(65) Prior Publication Data
US 2013/0150644 A1 Jun. 13, 2013

Related U.S. Application Data

(60) Provisional application No. 61/568,394, filed on Dec. 8, 2011.

(51) Int. Cl.
| C07C 4/04 | (2006.01) |
| C07C 4/02 | (2006.01) |
| C07C 2/02 | (2006.01) |
| C07C 11/00 | (2006.01) |
| F23L 15/02 | (2006.01) |
| B01J 19/02 | (2006.01) |
| B01J 19/24 | (2006.01) |
| B01J 4/00 | (2006.01) |

(Continued)

(52) U.S. Cl.
CPC . *C07C 4/04* (2013.01); *B01J 4/004* (2013.01); *B01J 8/0438* (2013.01); *B01J 8/0442* (2013.01); *B01J 8/0453* (2013.01); *B01J 8/0457* (2013.01); *B01J 19/02* (2013.01); *B01J 19/2485* (2013.01); *C10G 9/18* (2013.01); *C10G 9/26* (2013.01); *F23L 15/02* (2013.01); *B01J 2208/0053* (2013.01); *B01J 2208/00106* (2013.01); *B01J 2208/00309* (2013.01); *B01J 2208/00327* (2013.01); *B01J 2208/00495* (2013.01); *B01J 2208/00911* (2013.01); *B01J 2219/0004* (2013.01); *B01J 2219/00117* (2013.01); *B01J 2219/00121* (2013.01); *B01J 2219/00155* (2013.01); *B01J 2219/00159* (2013.01); *B01J 2219/0281* (2013.01); *B01J 2219/182* (2013.01); *B01J 2219/185* (2013.01); *B01J 2219/194* (2013.01); *B01J 2219/1923* (2013.01); *B01J 2219/1943* (2013.01); *B01J 2219/1947* (2013.01)

(58) Field of Classification Search
CPC ............ C07C 4/02; C07C 11/00; C07C 2/02; B01J 12/00
USPC ......................................... 585/650, 539, 402
See application file for complete search history.

(56) References Cited

U.S. PATENT DOCUMENTS 2,319,679 A 5/1943 Hasche et al.
2,678,339 A 5/1954 Harris
(Continued)

OTHER PUBLICATIONS

Stanford Research Institute's Process Economics Program Report No. 16, "Acetylene", 1966, pp. 8-9, 13-23, and 59-79.

*Primary Examiner* — In Suk Bullock
*Assistant Examiner* — Youngsul Jeong

(57) ABSTRACT

The present disclosure relates to reactor components and their use, e.g., in regenerative reactors. A process and apparatus for utilizing different wetted areas along the flow path of a fluid in a pyrolysis reactor, e.g., a thermally regenerating reactor, such as a regenerative, reverse-flow reactor, is described.

19 Claims, 2 Drawing Sheets

(51) Int. Cl.
  *B01J 8/04* (2006.01)
  *C10G 9/18* (2006.01)
  *C10G 9/26* (2006.01)
  *B01J 12/00* (2006.01)

(56) References Cited

U.S. PATENT DOCUMENTS

| | | |
|---|---|---|
| 2,692,131 A | 10/1954 | Hasche |
| 2,692,819 A | 10/1954 | Hasche et al. |
| 3,024,094 A | 3/1962 | Coberly |
| 3,093,697 A | 6/1963 | Kasbohm et al. |
| 7,815,873 B2 | 10/2010 | Sankaranarayanan et al. |
| 7,846,401 B2 | 12/2010 | Hershkowitz et al. |
| 7,906,010 B2 | 3/2011 | Keusenkothen et al. |
| 7,914,667 B2 | 3/2011 | Keusenkothen et al. |
| 7,943,808 B2 | 5/2011 | Hershkowitz et al. |
| 7,976,797 B2 | 7/2011 | Chun et al. |
| 8,119,076 B2 | 2/2012 | Keusenkothen et al. |
| 8,278,231 B2 | 10/2012 | Chun et al. |
| 8,303,803 B2 | 11/2012 | Keusenkothen et al. |
| 8,399,372 B2 | 3/2013 | Chun et al. |
| 2007/0191664 A1* | 8/2007 | Hershkowitz et al. ........ 585/539 |
| 2008/0142409 A1 | 6/2008 | Sankaranarayanan et al. |
| 2010/0290978 A1 | 11/2010 | Chun et al. |
| 2010/0292523 A1 | 11/2010 | Hershkowitz et al. |
| 2012/0111315 A1 | 5/2012 | Grenda et al. |

* cited by examiner

REACTOR COMPONENTS

PRIORITY

The present application claims priority to U.S. Ser. No. 61/568,394, filed on Dec. 8, 2011, entitled, "Reactor Components" the entire disclosures of which are hereby incorporated by reference herein.

FIELD OF THE INVENTION

The present disclosure relates to reactor components and their use in reactors. The present disclosure encompasses advanced materials, methods, and apparatus useful in regenerative pyrolysis reactors, such as may be used for pyrolyzing or cracking hydrocarbons. In one non-limiting example, the present disclosure relates to advanced use of wetted areas and associated materials, apparatus, and methods suitable for use in cracking hydrocarbon feeds in a high-severity pyrolysis reactor.

BACKGROUND OF THE INVENTION

Regenerative pyrolysis reactors may be utilized in pyrolyzing or cracking hydrocarbons. Regenerative reactor cycles are either symmetric (same chemistry or reaction in both directions) or asymmetric (chemistry or reaction changes with step in cycle). Examples of these reactors and the associated processes are described in U.S. Pat. Nos. 2,319,679; 2,678,339; 2,692,819; 3,024,094; 3,093,697; and 7,943,808. As one of the steps in the cycle, combustion can be used for regenerating reactors to perform cyclic, high temperature chemistry.

The process typically involves a heating step (e.g., regeneration step) and a pyrolysis step in different portions of a cycle. The heating step includes exothermic reactions, e.g., by conducting fuel and oxidant to a reaction zone, combusting the fuel and oxidant, and then conducting the combustion products away from the reaction zone. During the pyrolysis step, a feed containing hydrocarbons is conducted through the reaction zone, thereby pyrolyzing the hydrocarbons in the feed and conveying heat from a reactor bed or other source. Some regenerative pyrolysis reactors deliver fuel and/or oxidant directly to the combustion zone without having that stream pass through reactor beds that preheat the stream. The fuel and/or oxidant is typically introduced via nozzles, distributors, or burners that extend within the reactor using means generally perpendicular to the reaction flow direction and usually through the reactor vessel side wall. For example, during the heating step in a conventional Wulff cracking furnace, air flows axially through the regenerative bodies, and fuel is introduced via nozzles that extend within the side of the reactor, to combine with air (combusting and releasing heat) in an open region between regenerative bodies.

High-severity pyrolysis in regenerative pyrolysis reactors can result in high selectivity to acetylene that may be utilized for many dimensions of chemicals growth from natural gas and other hydrocarbon feeds. Accordingly, the capabilities of regenerative pyrolysis reactors or reverse-flow regenerative pyrolysis reactors suggest that these reactors may achieve the desired reaction conditions at extreme temperatures (e.g., greater than (>) 1700° C.) in a cost effective manner. That is, the higher temperatures within the reactor are preferred for high conversion of feeds to $C_2$ unsaturates. Particularly, conversions of 10 to methane greater than 50% (and reasonable selectivity) require temperatures >1400° C. and millisecond residence times. Longer residence times favor the formation of coke, an unwanted byproduct. For heavier hydrocarbons, the higher temperatures (e.g., >1400° C.) lessen heavy hydrocarbon co-product production, thereby simplifying the recovery stages of the process (e.g., fewer heavy co-products require less equipment to separate the co-products from the desired streams).

Operation of high severity hydrocarbon cracking processes and regenerative pyrolysis reactors involves various competing operational and engineering challenges. For example, as noted in U.S. Patent Pub. App. Nos. 2010/0290978 and 2010/0292523, the high temperatures can exceed the long term viability of conventional apparatus, including conventional ceramics. That is, the reactor components have to be thermally stable at these high temperatures.

While the high temperatures enhance selectivity to $C_2$ unsaturates, the rapid kinetics of high temperature operation mandate short residence times (e.g., milliseconds). As a result, high flow velocities of the streams through the reactor or use of shorter reactors are needed to provide these short residence times. Unfortunately, the high flow velocities increase pressure drop, which is yet another challenge for the operation of these reactors. Accordingly, the conventional approach is to reduce residence time by shortening the length of the reactor bed to provide short residence time without unduly high flow velocity. However, shortening the reactor bed while maintaining high productivity (e.g., volumetric flow rate) results in lowering the length to diameter ratio for the reactor, causing significant flow distribution challenges.

In addition, conventional techniques fail to adequately address the heat transfer rate within the reactor. The heat transfer rate involves convective heat transfer and radiant heat transfer, which are present for certain operating temperatures. Convective heat transfer has a rate that is proportional to surface area (e.g., wetted area, or transfer area per bed volume), while radiative heat transfer is emitted by gases and components within the reactor. Regenerative reactor efficiency is enhanced by increasing the rate of heat transfer. However, pressure drop (e.g., momentum transfer) is also proportional to the wetted area. Thus, conventional attempts to enhance reactor efficiency by increasing wetted area also result in increased pressure drop.

Accordingly, it is desired to enhance the flow of fluids through reactor in a manner that increases the efficiency of the process. Further, it is desired to have a reactor configuration that provides high heat transfer rates and short residence times without 10 to imposing process-limiting constraints of higher pressure drop. Also, it is desired to utilize the convective properties along with the radiative properties for certain portions and process flow components based on the temperature profile within the reactor to further enhance the operation of the process.

SUMMARY OF THE INVENTION

The present techniques relate to materials, methods, and apparatus useful in regenerative pyrolysis reactors, such as may be used for paralyzing or cracking hydrocarbons. The process utilizes one or more components within a reactor, which are configured to enhance the flow of streams through the reactor. These process flow components may include bed packings, such as multi or stage heat exchanger media or monoliths or other reactor internals.

In thermal pyrolysis, heat is exchanged via interaction between the surface area of the flow passages and the fluids within the reactor. The heat transfer within the reactor involves convective heat transfer and radiative heat transfer. We have discovered that the radiative heat transfer coefficient increases rapidly within the reactor at temperatures above about 700° C. The increase roughly doubles the overall heat transfer coefficient for every about 300° C. increase in temperature. This heat transfer mechanism may be utilized to further enhance the reactor and its operation.

To enhance performance of regenerative pyrolysis reactors and reverse flow regenerative pyrolysis reactors, the heat transfer rate may be adjusted to enable rapid quench and thus shorten residence times at high temperatures and increase reactor efficiency. To provide this enhancement, certain portions of the reactor (e.g., portion near the middle or zone of the maximum temperature) may rely upon radiative heat transfer, which is not as dependent on the surface area of a flow path. In other portions of the reactor (e.g., at the ends of the reactor), radiative heat transfer is less influential and convective heat transfer may dominate the heat transfer between fluids within the reactor and the surface area of the flow path. Accordingly, the volumetric or wetted area may be varied within the reactor (e.g., through the reactor beds along the flow path of the streams within the reactor), based on the temperature profile that occurs in that zone during operation, and based on the heat transfer mechanism. As a result, the surface area may be useful for convective heat transfer in certain zones of the reactor, while other zones of the reactor may depend less on surface area. Accordingly, the wetted area may vary for different portions of the reactor (e.g., different portions of the reactor bed, different reactor beds, or other process flow components at different locations in the reactor) at the respective locations to lessen the pressure drop and increase flow velocity.

In one or more embodiments, a hydrocarbon conversion method is described. The method comprises: passing a first mixture comprising hydrocarbons to a regenerative reactor, wherein the regenerative reactor has a first portion having a first plurality of flow passages with a wetted area $a_{v1}$, and a second portion having a second plurality of flow passages with a second wetted area $a_{v2}$; wherein the ratio of the second wetted area $a_{v2}$ to the first wetted area $a_{v1}$ is ≤0.75; reacting at least a portion of the hydrocarbons within the reactor to produce a second mixture comprising $C_2$ unsaturates. The reacting may include exposing the at least a portion of the hydrocarbons within the reactor to peak pyrolysis gas temperatures ≥1200° C. to produce the second mixture.

In yet another embodiment, a hydrocarbon pyrolysis reactor is described. The reactor comprises a housing, a plurality of input means and one or more insulation components and process flow components. The housing encloses an interior region and having one or more insulation components disposed adjacent to the housing. The plurality of input means is configured to manage the flow of one or more streams into the interior region from a location external to the interior region. The one or more process flow components are configured to manage the flow of fluids through the interior region, wherein the one or more process flow components comprise: (i) a first bed packing having a first plurality of flow passages and a first wetted area $a_{v1}$; and (ii) a second bed packing having a second plurality of flow passages and a second wetted area $a_{v2}$, wherein the ratio of the second wetted area $a_{v2}$ to the first wetted area $a_{v1}$ is ≤0.75. That is, the wetted areas are different (e.g., $a_{v1} \neq a_{v2}$) or $a_{v2}$ is different from $a_{v1}$ by at least 25% of the larger wetted area $a_{v1}$ or $a_{v2}$.

In other embodiments, the ratio of the second wetted area $a_{v2}$ to the first wetted area $a_{v1}$ is ≤0.75 or ≤0.5, or may be in the range of 0.05 to 0.75 or even in the range of 0.10 to 0.50. The first portion of the reactor bed is a first monolith and the first wetted area $a_{v1}$ is in a range of 800 m$^{-1}$ to 3000 m$^{-1}$ or 500 m$^{-1}$ to 4000 m$^{-1}$, wherein the second portion of the reactor bed is a second monolith and the second wetted area $a_{v2}$ is in the range of 100 m$^{-1}$ to 800 m$^{-1}$ or 100 m$^{-1}$ to 1000 m$^{-1}$. The method may include calculating the ratio by the following equation:

$$R_{21} = a_{v2}/a_{v1} = X^{(T2-T1)/300}$$

wherein $R_{21}$ is the ratio, $T_2$ is the zone temperature of the second portion in units of ° C., $T_1$ is the zone temperature of the first portion in units of ° C., and the X parameter is between 0.1 and 0.9 or in the range of 0.25 to 0.75; obtaining the first portion and the second portion based on the determined ratio $R_{21}$; and disposing the first portion and second portion within to the reactor.

In one or more of the embodiments, a mixing means may be utilized. For instance, the mixing means may be disposed (i) between the first portion of the bed packing and the second portion of the bed packing or (ii) adjacent to the second portion of the bed packing. The mixing means may comprise one or more mixing components, such as one or more is different plates, or consist essentially of a gap. In one or more of the embodiments, a mixing means may be disposed between first and second reactors and one or both of the first and second reactors may comprise one or more portions of reactor beds which portions have wetted area that is adjusted according to the temperature of the respective portion.

In other embodiments, additional portions of the reactor or reactor bed may include different wetted areas. For instance, the reactor may have a third portion having a third plurality of flow passages with a wetted area $a_{v3}$, wherein the ratio of the third wetted area $a_{v3}$ to the second wetted area $a_{v2}$ is ≤0.75. Further, the reactor may include a fourth portion having a fourth plurality of flow passages with a fourth wetted area $a_{v4}$, wherein the ratio of the fourth wetted area $a_{v4}$ to the third wetted area $a_{v3}$ is ≤0.75. In another embodiment, the regenerative reactor has a third portion having a third plurality of flow passages with a third wetted area $a_{v3}$, and has a fourth portion having a fourth plurality of flow passages with a fourth wetted area $a_{v4}$, wherein the ratio of the third wetted area $a_{v3}$ to the fourth wetted area $a_{v4}$ is ≤0.75; and further comprising passing at least one of the first mixture and the second mixture through the third portion and the fourth portion. In yet another embodiment, the reactor has a third portion having a third plurality of flow passages with a third wetted area $a_{v3}$, and has a fourth portion having a fourth plurality of flow passages with a fourth wetted area $a_{v4}$, wherein the ratio of the third wetted area $a_{v3}$ to the fourth wetted area $a_{v4}$ is ≤0.75 and the ratio of the third wetted area $a_{v3}$ to the second wetted area $a_{v2}$ is in the range of 0.8 to 1.2. Each of these may include passing at least one of the first mixture and the second mixture through the third portion and/or the fourth portion.

In yet other embodiments, the reactor may be formed from specific materials. For instance, one or more of the bed packings (e.g., a first portion and a second portion of the reactor bed) may comprise yttria ($Y_2O_3$) for ≥50 wt % of the total weight of the respective portion of the reactor bed. In another embodiment, one or more of the bed packings (e.g., a first portion and a second portion of the reactor bed) comprises from 0.001 wt % to 5 wt % of compounds that comprise elements selected from the group consisting of Al, Si, Mg, Ca, Fe, Mn, Ni, Co, Cr, Ti, Hf, V, Nb, Ta, Mo, W, Sc, La, and Ce, and mixtures thereof based upon to the weight of the respective portion of the reactor bed.

Figure 1A:
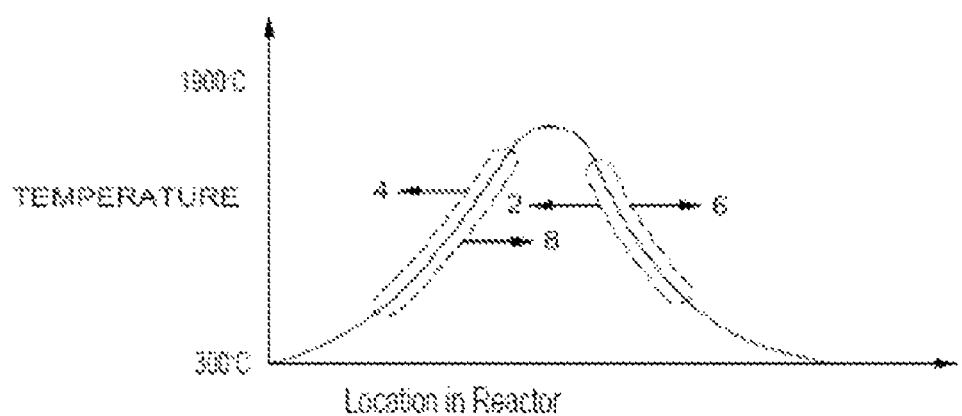
FIGS. 1A and 1B schematically illustrate thermal regeneration in a reverse flow reactor and associated temperature profile.

Although the invention is described in terms of a thermal pyrolysis process for producing acetylene and ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE PREFERRED EMBODIMENTS

The present disclosure is based in part on the observation that reactor components, such as insulation and process flow components are utilized in different zones within a reactor, e.g., those described in U.S. Pat. No. 7,943,808 and U.S. Patent Pub. App. Nos. 2010/0290978 and 2010/0292523. The process flow components may include components that manage the flow of process fluids through the internal zones within the reactor and store and release heat to the process fluids, while the insulation components may include components that inhibit the heat transfer from the interior of the reactor to locations external to the reactor, which may also inhibit the flow of process fluids to locations external to the reactor. The reactor components are sensitive to (a) environmental operating conditions; (b) temperature operating conditions; and/or (c) heat transfer properties based on the location within the reactor. In the reactor, heat transfer concerns the exchange of thermal energy from one material to another (e.g., between a fluid and the passages containing the fluid), which may be based on conduction, convection, radiation, and/or chemical reaction. Accordingly, these different components may include different materials having different compositions and/or properties, which are utilized at certain locations based on the conditions for that location and the intended use at that location. Accordingly, the reactor components are formed of materials for these specific locations, which may include maintaining integrity, functionality, and withstanding long term exposure to temperatures $\geq 1200°$ C., preferably $\geq 1500°$ C., more preferably $\geq 1700°$ C., and even more preferably $\geq 2000°$ C. for operating margin.

We have discovered that the radiative heat transfer coefficient increases rapidly within the reactor at temperatures above about 700° C. The increase roughly doubles the overall heat transfer coefficient for about every 300° C. increase in temperature. Thus, the different portions of the reactor may be configured to utilize the different heat transfer mechanisms within the reactor.

Within the reactor, different steps and locations may be influenced by these different heat transfer mechanisms. Accordingly, in one or more embodiments, the different steps in a cycle may be utilized to enhance the conversion process based on the heat transfer mechanisms. For instance, during a heating step, combustion reactions may produce heat via chemical reaction, which heat is transferred into the reactor components via convection, conduction and/or radiation, while the pyrolysis step may involve endothermic reactions that remove heat from the reactor components via convection, conduction, and/or radiation. To enhance the conversion of the hydrocarbons, the reactor components may be configured to facilitate efficient heat transfer rates at various locations within the reactor based on the heat transfer mechanism. For instance, convection (e.g., the transfer of heat from one place to another by movement of fluids) and conduction (e.g., energy emitted exchange of kinetic energy of particles) tend to dominate the heat transfer within the cooler portions of the reactor or reactor components that are nearer the ends of the reactors. In the hotter portions near the center of the reactor, thermal radiant (e.g., energy emitted by matter as electromagnetic waves) tend to dominate the heat transfer within the reactor.

In addition, the reactor design presents a compromise between pressure drop and heat transfer efficiency with higher packing wetted areas providing both higher pressure drop and efficiency. High efficiency makes a process more economical by reducing fuel costs. However, high pressure drop results in the use of reactors with low length/diameter (L/D) ratios. These configurations encounter difficulties in flow distribution that can result in poor selectivity and poor economic performance.

We have discovered that the radiation-assisted heat transfer may be utilized to reduce the wetted area in areas of higher temperature, which reduces the pressure drop in these zones. As a general guideline, volumetric wetted area ($a_v$) can be reduced by a factor of two for about every 300° C. increase in temperature above 700° C. That is, the pressure drop (e.g., momentum transfer rate) can be reduced without proportional reduction of heat transfer rate by introducing a variation in the wetted area of the process flow components along the length of the reactor at certain locations. In this manner, high reactor efficiency and selectivity is maintained at lower pressure drops, enabling more cost-effective and higher-performing reactors having a higher L/D ratio. Specifically, the wetted area is decreased, reducing momentum transfer rate in zones having high temperature, such that radiative heat transfer rates supplement convective heat transfer rates.

Measurement and calculation of wetted area of bed packing is well known in the art. The term "wetted area", as used herein, means volumetric wetted area, and is the amount of heat transfer surface that is available per unit volume of reactor bed. It has units of area/volume, which is equivalent to units of 1/length, or length$^{-1}$. For a reactor bed containing spherical particles, $a_v$ is equal to $6(1-\epsilon)/D$, where $\epsilon$ is the void fraction of the bed and D is the average particle diameter. For a bed of parallel-channel honeycomb material, wetted area is characterized in terms of a channel density (e.g., cells per area or cells per square inch (cpsi)) and channel width D and the $a_v$ formula depends on the shape of the cells. For instance, for square cells on a square grid, the wetted area, $a_v$ =4D (cells/area). As such, the wetted area may be calculated differently for different configurations of the reactor bed.

In one or more embodiments, process flow components may utilize different wetted areas (e.g., staged monoliths with different wetted areas or other particulate packing, such as pebble beds). The different wetted areas may lessen pressure drop by utilizing the different heat transfer properties based on the heat transfer mechanism that dominates a specific location. As an example, near the middle of the reactor (e.g., a zone of the reactor exposed to maximum temperatures), radiative heat transfer may dominate the heat transfer properties, so a lower surface area monolith (e.g., lower cpsi honeycomb) or lower wetted-area particulate packing or tile configuration may be used if it has acceptable optical properties, such as sufficiently high emissivity to provide good radiative heat transfer. At the cooler ends of the reactor, radiative heat transfer is not as influential, and materials with higher surface area for heat transfer or higher cpsi honeycombs are preferentially used (e.g., conductive heat transfer and convective heat transfer properties are preferred). The wetted area at different locations in the reactor may preferentially lead to using different wetted areas (e.g., monolith surface areas) at various reactor locations along the flow path, which may lessen pressure drop.

As an example, the preferred wetted area selections may be staged from ends to the center of the reactor for one or more reactor beds based on the temperature profile within the reactor and the heat transfer properties. In the cooler ends of the reactor, materials that have the higher convective and conductive heat transfer are preferred. Because convective heat transfer and conductive heat transfer at the cooler ends of the reactor are more influential, the wetted area may be higher relative other portions of the reactor. At higher temperature zones in the reactor (e.g., towards the center of the reactor), the radiative heat transfer may dominate the convective heat transfer and conductive heat transfer. That is, at the center of the reactor, the components may have to withstand the maximum temperatures (e.g., >1700° C. or >2000° C.). At the elevated temperatures, radiative heat transfer dominates other heat transfers, and reactor components of ceramic materials that have better radiative heat transfer properties, such as higher emissivities, may be preferred. Also, the reactor components should perform other functions besides heat exchange, such as manage the flow of fluids through the reactor, provide support, etc. As such, the wetted area in the higher temperature zones (e.g., towards the center of the reactor) may be lower relative other portions of the reactor.

To provide proper heat transfer for the intended use, the wetted areas utilized for the reactor components may be selected to enhance certain characteristics. For instance, the reactor components used in a regenerative reactor may have various wetted areas that are in the range of $10 \, m^{-1}$ and $10,000 \, m^{-1}$, in the range of $330 \, m^{-1}$ and $6500 \, m^{-1}$, or in the range of $400 \, m^{-1}$ and $4000 \, m^{-1}$.

Further, the reactor components may be selected of materials that have certain properties, such as chemical stability and thermal stability, for example, which are useful in the operation of the reactor. That is, the different materials may be utilized within certain locations based on the exposure to certain temperatures, certain reactions and chemistries based on the location within the reactor. As an example, refractory material may be a ceramic, which may include yttria, zirconia, alumina (oxides and/or carbides) and/or other refractory material capable of withstanding temperatures within the reactor. The term "refractory material" means a material having chemical and physical properties that are able to withstand temperatures above 538° C., which are typically utilized in structures, or as components of systems, such as furnaces or reactors. As a specific example, the process flow components and insulation components near the zone where exothermic reactions are performed may include reactor components comprised of yttria. Specifically, these components may be high-yttria refractory materials comprising yttria $(Y_2O_3) \geq 50$ wt %, $\geq 70$ wt %, $\geq 90$ wt %, or $\geq 95$ wt % of the total weight of the reactor component and having a pyrometric cone equivalent of $\geq 1600°$ C. Other reactor components may include metals and/or other ceramics, which may be located near the ends of the reactor or outside of a certain temperature range. These materials may include stabilized zirconia, which may include a multi-modal formulation for stabilized zirconia to create a durable porosity (30% to 45%) and/or a dual-oxide composition that combines small particle stabilizer with coarse-particle partially stabilized zirconia (PSZ). One such reactor will now be described in more detail, but the present invention is not limited thereto, and this description is not meant to foreclose other embodiments within the broader scope of the present invention.

I. Reactor Apparatus and Process

In the present disclosure, a reactor refers to equipment used for chemical conversion. As such, several items identified as reactors may be combined to become a single entity that is also identified as a reactor, in that individual and combined entities may be characterized as equipment used for chemical conversion. The terms "pyrolysis" and "pyrolysis chemistry" mean an endothermic reaction conducted at a temperature sufficient for thermally breaking C—C or C—H bonds, optionally aided by a catalyst, e.g., the conversion of hydrocarbons to unsaturates, such as ethylene and acetylene.

The terms "reactor", "reactor system", "regenerator", "recuperator", "regenerative bed", "monolith", "honeycomb", "reactant", "fuel", and "oxidant" have the meanings disclosed in U.S. Pat. No. 7,943,808, which is incorporated by reference herein in its entirety. The term "pyrolysis reactor", as used herein, refers to a reactor, or combination or system thereof for converting hydrocarbons by at least pyrolysis. A pyrolysis reactor optionally includes one or more reactors and/or associated equipment and lines. The term pyrolysis reactor encompasses, e.g., the combination and system of first and second pyrolysis reactors described in U.S. Patent App. Pub. No. 2007/0191664. Other examples are described in U.S. Pat. No. 7,491,250, U.S. Patent Ser. No. 61/349,464 and U.S. Patent App. Pub. Nos. 2007/0144940 and 2008/0142409. With respect to pyrolysis reactors, the term "residence time" means the average time duration for non-reacting (non-converting by pyrolysis) molecules (such as He, $N_2$, Ar) having a molecular weight in the range of 4 to 40 to traverse the reactor or a defined zone within the reactor, such as a pyrolysis zone of a pyrolysis reactor. The term "pyrolysis stage" means at least one pyrolysis reactor, and optionally including means for conducting one or more feeds thereto and/or one or more products away therefrom. With respect to reactors, the term "zone" or "region" means a location within a reactor, e.g., a specific volume within a reactor and/or a specific volume between two reactors. A "pyrolysis zone" is a volume within the reactor for conducting pyrolysis. The term "thermal pyrolysis" means <50.0% of the heat utilized by the pyrolysis is provided by (a) by exothermically reacting an oxidant with hydrocarbon and/or hydrogen of the first mixture and/or (b) contacting the first mixture with the gaseous and/or liquid products of combustion to heat the first mixture. The term "thermal pyrolysis reactor" means a pyrolysis reactor wherein $\geq 50.0\%$ of the heat utilized by the pyrolysis is provided by heat transfer from reactor components, e.g., solid surfaces associated with the reactor, such as tubulars or bed materials; optionally $\geq 80.0\%$ or $\geq 90.0\%$ of the heat utilized by the pyrolysis is provided by such heat transfer. Optionally, an exothermic reaction (e.g., combustion) occurs within the thermal pyrolysis reactor, the exothermic reaction providing a major amount (i.e., $\geq 50.0\%$) of the endothermic heat of pyrolysis, such as $\geq 75.0\%$ or $\geq 90.0\%$ thereof. The term "high-severity" with respect to the pyrolysis of a feed comprising hydrocarbon, e.g., the first mixture means pyrolysis operating conditions resulting in the conversion to acetylene of $\geq 10.0$ wt % of the feed's hydrocarbons based on the total weight of hydrocarbons in the feed.

Regenerative pyrolysis reactors are known and conventionally used for converting or cracking reactions, and to execute cyclic, high temperature chemistry, such as those reactions that may be performed at temperatures higher than can suitably be performed in conventional steam crackers. Regenerative reactor cycles typically are either symmetric or asymmetric. Asymmetric cycles are typically used to execute endothermic chemistry, and the desired endothermic chemistry is paired with a different chemistry that is exothermic (typically combustion) to provide heat of reaction for the endothermic reaction. In this embodiment, the regenerative, reverse-flow pyrolysis reactor is (i) "reverse flow" in the sense that upstream region of the reactor with respect to the average flow of the first mixture is the downstream region with respect to the average flow of the fourth mixture and (ii) "regenerative" in the sense that at least a portion of the heat consumed during the conversion of the first mixture is provided by exothermically reacting the fourth mixture. Regenerative reactor being a reactor that exothermically reacts fuel and oxidant to store heat within a defined volume in a heating step and removes a portion of the heat during the conversion of a feed stream in a conversion step in sequential steps. For example, under thermal pyrolysis conditions, the regenerative reactor exothermically reacts fuel and oxidant to store heat within a defined volume (e.g., reactor bed) in a heating step and removes a portion of the heat during the conversion of a pyrolysis stream in a pyrolysis step.

Accordingly, as it may be appreciated, a variety of regenerative pyrolysis reactors may be utilized. For example, a hydrocarbon pyrolysis reactor may include a housing, a plurality of input means (e.g., conduits and valves), one or more insulation components (e.g., insulation bricks) and one or more process flow components (e.g., reactor beds, mixing components, etc.). The housing may be utilized to enclose an interior region and has one or more insulation components disposed adjacent to the housing. The plurality of input means 10 to may include one or more conduits and one or more valves that are configured to manage the flow of one or more streams into the interior region from a location external to the interior region or housing. The one or more process flow components are configured to manage the flow of fluids through the interior region, wherein the one or more process flow components may include a reactor bed having different portions with each having different flow passages and a wetted area. Specifically, as noted further below, the reactor bed may include (i) a first portion comprising a first plurality of flow passages and having a first wetted area $a_{v1}$; and (ii) a second portion comprising a second plurality of flow passages and having a second wetted area $a_{v2}$, wherein (i) $a_{v1} \neq a_{v2}$ and (ii) $a_{v2}$ is different from $a_{v1}$ by at least 25%. The difference percentage for $a_v$, as used herein, is defined to be based on the higher of the two wetted areas. For example, if $a_{v1} \geq a_{v2}$, then the percent difference between $a_{v1}$ and $a_{v2}$ is $100*(a_{v1}-a_{v2})/a_{v1}$.

Regenerative reverse-flow reactors may involve multiple steps repeated in sequence to form a cycle for the process. That is, the pyrolysis process may include two or more sequential steps, which include a regeneration step to heat the zones and a pyrolysis step that converts the hydrocarbons in a first mixture into a second mixture (e.g., reactor products) during a hydrocarbon processing mode. The steps may involve passing mixtures over a solid material in fixed orientation (e.g., one or more reactor beds). As part of these steps, valves may be utilized to alternate introduction of hydrocarbons in a first mixture and/or fourth mixture into the interior region of the reactor. As an example, regenerative reactors typically deliver a fourth mixture (e.g., combustion reactants) of fuel, oxidant, and/or a supplemental amount of one of these reactants, directly to a location along the flow path within the reactor (e.g., a mixing zone). The delivered reactants in the fourth mixture then exothermically react (combust) therein and heat the process flow components. Thereafter, the fifth mixture (e.g., exothermic reaction products, such as combustion products) is exhausted and a first mixture, such as vaporized hydrocarbons, is introduced into the reactor to flow in the opposite direction, and exposed to the heated process flow components to cause heating and pyrolysis of the hydrocarbons in the first mixture. The second mixture (e.g., pyrolyzed reaction products and/or unreacted first mixture) is then quenched as they flow through the reactor to halt the pyrolysis reactions and yield pyrolysis products (e.g., reactor products). During the quenching, the process flow components (e.g., reactor beds) absorb heat from the second mixture, sufficient to impart heat into the fourth mixture when the flow is again reversed.

The high-severity operating conditions may include peak pyrolysis gas temperatures between 1200° C. and 2200° C., preferably between 1400° C. and 1900° C. In 10 to particular, for reactors with an isothermal temperature profile, the temperatures may be between 1450° C. and 1700° C., or between 1540° C. and 1650° C. For reactors with a Gaussian-like temperature profile, the peak pyrolysis gas temperatures may be in the range of 1540° C. to 2200° C. or 1600° C. to 1800° C. Further, the preferred operating pressures may include pressures ≥4 pounds per square inch gauge (psig) (28 kilo Pascals gauge (kPag)), ≥15 psig (103 kPag), ≥36 psig (248 kPag), ≥44 psig (303 kPag), or ≥103 psig (710 kPag), but may be ≤300 psig (2068 kPag), ≤163 psig (1124 kPag), or ≤150 psig (1034 kPag). Residence times in the pyrolysis reactor may be ≤0.5 second, ≤0.3 second and preferably ≤about 50 milliseconds or in the range of 0.001 seconds to 1.0 seconds or in the range of 0.5 second and 0.001 second. For a regenerative reactor, the process may operate at cycle times in the range of 1 second to 240 seconds, in the range of 1 second to 60 seconds, in the range of 2 seconds to 40 seconds, in the range of 2 seconds to 20 seconds, or even in the range of 3 seconds to 10 seconds.

Also, as may be appreciated, these different pressures and temperatures may be utilized together to form different combinations depending on the specific configuration of equipment. Further, for a regenerative reverse flow reactor, the pressure in the pyrolysis step may be similar or different to the pressure in the regeneration step (e.g., at lower or higher pressure than the pyrolysis step).

The regeneration step has different temperature profiles along the flow path at different locations within the reactor for each of the steps. The shape of that profile depends on many factors, including if and where a heat release reaction (combustion) occurs, the initial temperature distribution, the duration of the regeneration step, the flow rate and inlet temperature of the gas stream, and the heat capacity and transfer properties of the gas and solid material. On average, the solid material is hottest at the end of the regeneration step. The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors do not operate in the steady state. That is, at any given location, the temperature changes. However, these reactors may be in a periodic steady state, meaning that the same cycling of temperatures occurs over and over as the reactor sequentially repeats the regeneration and pyrolysis steps.

The reactor may include reactor components, such as process flow components (e.g., reactor components used to manage the flow of mixtures through the reactor, such as a reactor bed and/or mixing component) and insulation components (e.g., reactor components used to manage the heat transfer from the process flow within the reactor to the external surface of the reactor, such as insulation bricks, tiles or packing). The reactor components may be formed from different materials, such as refractory materials. The heat generated from the regeneration step may preferably be stored in a process flow component of a refractory material, such as a reactor bed, mixing component and/or other solid material. The process flow component's material may be designed to facilitate storage and utilization of heat. Checker bricks, tiles, and monoliths may be used as the process flow components within the reactor. Such materials form a network of passages that are used by the gases in each step to transit the region containing solid material. The refractory material of the process flow components may be a ceramic, which may include yttria, zirconia, alumina, and/or other refractory material capable of withstanding temperatures within the pyrolysis reactor.

In an embodiment, one or more of the reactor beds include separate passages through reactor components to manage the flow of hydrocarbon components of the first and/or fourth mixtures through the reactor beds. Preferably, each reactor bed includes separate passages. The separate flow passages in the reactor beds can further comprise flow barriers that effectively function as walls to lessen or prevent cross flow or mixing of fluids between passages. Each reactor bed preferably includes multiple passages, which may preferably be in parallel flow arrangement. The channeled reactor bed may preferably be comprised of one or more honeycomb monoliths. Preferred honeycomb monoliths are structures that comprise many (e.g., a plurality, meaning more than one) gas flow passages, arranged in parallel fashion with walls serving to separate each passage. Such reactor can include a single monolith or a plurality of monoliths. Each monolith can be formed by extruding or die pressing monolith blocks with shaped (e.g., square or hexagonal) cross-section and two- or three-dimensionally stacking, such blocks above, behind, and beside each other. Monoliths are particularly effective as reactor beds because they provide high heat transfer capacity with lessened pressure drop.

Figure 1B:
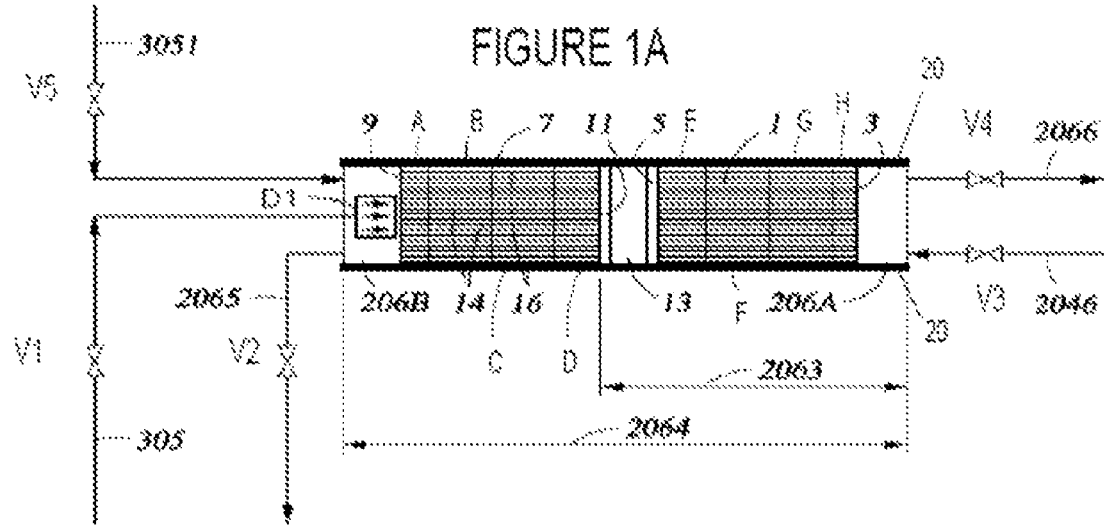

An exemplary embodiment of a reverse-flow regenerative reactor utilized for a two-step asymmetric cycle reaction is depicted in FIG. 1B with the temperature profile depicted in FIG. 1A, which are discussed together for simplicity. The system comprises two reactors: a first (recuperator/quenching) reactor 7 and a second (pyrolysis/reforming) reactor 1. The first reactor 7 may be divided into different zones A, B, C, and D, while the second reactor is divided into zones E, F, G, and H. Each of these zones has a respective wetted surface area for passages or channels through the respective zone. Accordingly, these different wetted surface areas may be utilized to enhance the operation of the regenerative reactor.

The first reactor 7 and second reactor 1 can include, e.g., one or more conduits, channels, or passages. The term "conduit" refers to means for conducting a composition from one location to another. The term encompasses (i) elementary conducting means, such as a pipe or tube, and (ii) complex means such as tortuous pathways through conducting means, e.g., pipes, tubes, valves, and reactors, that are filled with random packing. The term "passage" means a geometrically contiguous volume element that can be utilized for conveying a fluid within a reactor, regenerator, recuperator, regenerative bed, monolith, honeycomb, etc. The term "channel" means a plurality of passages that can be utilized together for conveying a fluid within the reactor, regenerator, recuperator, regenerative bed, monolith, honeycomb, etc. For example, a honeycomb monolith can comprise a single channel, the channel having a plurality of passages or sets of passages, e.g., hundreds of thousands of passages per square meter of the honeycomb's cross-section.

The first reactor 7 and second reactor 1 comprise reactor beds, the reactor beds comprising bedding or packing material, such as one or more of glass or ceramic beads or spheres; metal beads or spheres; (i) ceramic, including, e.g., alumina, silica, yttria, zirconia, etc., and mixtures thereof; or (ii) metal honeycomb materials; ceramic tubes; extruded monoliths catalysts; etc. The materials comprising the reactor bed are selected to maintain integrity, functionality, and withstand long term exposure to temperatures ≥700° C., e.g., ≥1200° C., such as ≥1500° C., or even ≥2000° C. for operating margin. The operation and configuration of the first and second reactors can be, e.g., the same as those described in U.S. Pat. No. 7,943,808. The shape of the reactor beds is not restricted to any particular geometry. For example, the first and second reactors can be elongated, and can have elliptical, cylindrical, and/or rectangular cross-sections, including combinations thereof. The reactors can be of the same shape and size, but this is not required. For example, the first reactor can be in the form of a honeycomb monolith of substantially cylindrical cross-sections. The first reactor's channels each comprise a plurality of passages, the passages comprising substantially parallel, substantially independent flow-paths within the regenerative media, e.g., within the honeycomb. The passages within a portion (e.g., one or more of zones A-D or E-H) of the reactor can each be of the same size, shape, and AP, for example.

As noted above, reactors 1 and 7 may be divided into regions or zones A-D and E-H. A region or zone has a beginning and end represented by a plane or surface that is roughly orthogonal to net flow direction and a region or zone has a characteristic "zone temperature" that is an average over all locations in the zone and an average over any periodic temperature changes that occur due to reverse-flow reactor operation. Zone temperature can be measured is or predicted, as is well known in the art. There need not be any physical manifestation within the reactor of the zone's beginning or end. It may simply be a mathematical construct defining region within an otherwise homogenous reactor bed. Within any zone, the reactor bed contents can be characterized in terms of volumetric wetted area ($a_v$). If the zone is homogenous in contents, $a_v$ will be constant throughout the zone. If the zone is inhomogeneous, then $a_v$ should be taken as a volume average over the zone.

Reactor bed contents are typically characterized in terms of tortuosity ($\tau$), void fraction ($\epsilon$) and wetted area ($a_v$). Tortuosity tends to impact the momentum transfer rate more than the heat transfer rate, so low tortuosity packing (e.g., straight channel honeycombs) tends to be preferred. Void fraction determines the ratio of heat-storing solids in the bed relative to the gas-carrying passages, and it can be adjusted over a wide range without impacting the heat transfer rate or momentum transfer rate. Wetted area directly relates to certain heat transfer properties, such as convective heat transfer and conductive heat transfer, while also directly relates to the momentum transfer rate. The impact of wetted area is similar for convective heat transfer and momentum transfer rate. Thus, for reactors employing conventional convective heat transfer, the selection of wetted area provides a design tradeoff between high heat transfer (efficiency and selectivity) versus high momentum transfer, which manifests as pressure drop (e.g., resulting in poor L/D and difficult reactor design).

However, the proposed techniques may utilize different wetted areas based on the dominant heat transfer mode at the location within the reactor, such as within a specific zone. For example, a first portion of a reactor bed (e.g., zones A and B of reactor 7) may include various flow passages having a wetted area $a_{v1}$, while a second portion of the reactor bed (e.g., zones C and D) may include other flow passages having a second wetted area $a_{v2}$. The wetted areas $a_{v1}$ and $a_{v2}$ may not be equal (e.g., $a_{v1} \neq a_{v2}$) and may include wetter areas $a_{v1}$ and $a_{v2}$ being different from each other by at least 25%, at least 30%, at least 40% or at least 50%.

In one or more embodiments, reactor beds have cool ends (e.g., end 9 of reactor 7 or end 3 of reactor 1) that have average temperatures below 700° C. Thus, one can identify a "base zone" within reactor 1 or 7 that has a zone temperature $T_B$ that is near 700° C., such as between about 600° C. and 800° C. This base zone may include reactor contents that have a wide range of temperatures (e.g., 300° C. to 1000° C.) or a narrow range of temperatures (e.g., 650° C. to 750° C.). The base zone may be homogeneous or inhomogeneous, but is preferably a region of constant wetted area. The average volumetric wetted area of the base zone is designated as $a_{vb}$. Base-zone wetted area in reactor beds may be between 10 m$^{-1}$ and 10,000 m$^{-1}$, e.g., between 330 m$^{-1}$ and 6500 m$^{-1}$, 500 m$^{-1}$ and 4000 m$^{-1}$, 800 m$^{-1}$ and 3000 m$^{-1}$.

Additional zones through the reactor may also be identified. For instance, zone j (e.g., where 'j' denotes zones B, C, G and/or any other zone) may be a zone within reactor 1 or 7 that has a zone temperature $T_j$ that is near 1000° C., such as temperatures in the range of about 800° C. and 1200° C. or in the range of 900° C. to 1100° C. Another zone j may have a zone temperature $T_j$ that is greater than or equal to ($\geq$) 1200° C., $\geq$1500° C. or $\geq$1700° C., such as temperatures in the range of about 1200° C. and 1800° C., in the range of 1400° C. to 1700° C. or in the range of 1500° C. to 1700° C. (e.g., for j denoting zone D or E). These zones may be homogeneous or inhomogeneous, but is preferably a region of constant wetted area. The average volumetric wetted area of any zone j is designated as $a_{vj}$. The wetted area in any zone j may be between 10 m$^{-1}$ and 10,000 m$^{-1}$, between 330 m$^{-1}$ and 6500 m$^{-1}$, or 400 m$^{-1}$ and 4000 m$^{-1}$ or 100 m$^{-1}$ and 1000 m$^{-1}$.

As noted above, one or more embodiments of the regenerative pyrolysis reactor can be divided into multiple non-overlapping zones A-D and E-H. In this embodiment, the reactor may include at least one base zone, such as zones A, B and/or H, having zone temperature $T_B$ that is between about 600° C. and 800° C. and having base zone contents with a wetted area of $a_{vb}$. In this embodiment, other zones (j), such as zones C, D, E, F, and G have zone temperature $T_j$ higher than $T_B$. In this embodiment, one or more of these higher-temperature zones (j) comprise bed packing whose wetted area is less than that of the base zone, with the reduction of wetted area characterized by the ratio ($R_{jb}$), which is the ratio of the wetted area in any zone j divided by the wetted area in the base zone (e.g., $R_{jb} = a_{vj}/a_{vb}$). In this embodiment, the higher-temperature zone (j) may be designed to have a wetted area $a_{vj}$ of zone j that is indicated by the following equation (e1):

$$R_{jb} = a_{vj}/a_{vb} = X^{(T_j - T_B)/300} \tag{e1}$$

where $T_j$ and $T_B$ are in units of ° C., and the X parameter is between 0.1 and 0.9, between 0.25 and 0.75, or preferably between 0.4 and 0.6. This same nomenclature may be used for any two zones, for example, the ratio may be referred to as ratio $R_{21}$ for a first zone 1 and a second zone 2. As long as both zones are at temperatures similar to or higher than a base zone temperature, equation (e1) may be used to provide a value for $R_{21}$.

As may be appreciated, the actual bed packing that may be available for use may vary based on the manufacturing methods (e.g., less than 25% or less than 10%) from a design target wetted area and still be suitable for use in the designated zone (j). As an example, the wetted area ratio ($R_{ij}$) between a hotter zone (i) having wetted area $a_{vi}$ and a cooler zone (j) having wetted area $a_{vj}$, may be calculated as $a_{vi}/a_{vj}$ and may have a value that is $\leq$0.75, $\leq$0.7, $\leq$0.6, or $\leq$0.5. In certain embodiments, the ratios between adjacent wetted areas may be in the range of 0.75 to 0.05, in the range of 0.7 to 0.075 or in the range of 0.5 to 0.1. The role of emissivity need not be considered in the design equation because most high temperature refractory materials have similar emissivities at high temperature. Emissivity has the effect of increasing the radiative heat transfer. Thus, if one employs a material with high emissivity in a hot zone, then it may be possible to further reduce the wetted area of that zone. Such conditions may be specified by the design equation (e1) by the use of a value of X between about 0.1 and 0.5, such as between about 0.3 and 0.45.

In another embodiment, one or more zones j may have a zone temperature $T_j$ that is lower than $T_B$ (e.g., temperature less than about 600° C. to 800° C.). Such zones may have reactor bed contents with wetted area $a_{vj}$ that is similar to or larger than $a_{vb}$, e.g., having a value between 50% and 400% of $a_{vb}$, such as between 75% and 150% of $a_{vb}$. Such differences in wetted areas are not employed to take advantage of radiative effects, but may be employed for other reasons, such as the opportunity to change materials in a colder region of the bed. For instance, the end portions of the reactor may include metal. That is, the materials may be adjusted for different zones of the reactor. For example, zones having temperatures below about 500° C. might be fabricated using metal packing or metal honeycombs that are not refractory in nature, but are nonetheless suitable in these lower temperature zones of the reactor.

As an example, the flow passages may be within one or more monoliths or flow passages through a reactor bed having two different types of bed packing adjacent to each other. For instance, the reactors 1 and 7 may include multiple reactor portions associated with the different zones A-D and E-H.

To operate, various steps may be performed as part of a cycle. For instance, in a heating step, $\geq$50.0 wt %, e.g., $\geq$75.0 wt %, such as $\geq$90.0 wt % of a first and second reactants are conducted separately to region 2063 by a portion of the channels 14 and 16. Each of channels 14 and 16 comprise a set of flow passages that collectively serve as substantially independent flow conduction means for the channel as it traverses the first reactor 7. The 10 to isolation or independence of these channels is substantially preserved as flow passes between any zones in first reactor 7. Preservation of this independence is typically maintained by choosing a packing passage size (e.g., honeycomb passage size) that is much smaller than the smallest cross-sectional dimension of the contiguous flow region that is conducting the first or second reactant. Because a given channel 14 or 16 traverses the entire reactor 7, it necessarily traverses zones A-D, and thus is comprised of passages that may have different characteristic $a_v$ in the different zones being traversed. Optionally, the first reactor 7 further comprises means for supplying additional fuel to region 2063, e.g., by a first-reactant conduit (not shown) external to first reactor 7 and/or a first-reactant channel (not shown) located within first reactor 7. Optionally, such means are utilized solely for conducting the additional fuel (as, e.g., first reactant) toward region 2063.

Optionally, one or more mixer means are used between the first and second reactors to improve the oxidation reaction (e.g., combustion reaction). Mixer mechanism, distributor mechanism, reactor system internals, flow-control mechanisms, etc., for the reactor can be substantially the same as those described in U.S. Pat. No. 7,943,808, for example.

It is understood that one or more of valves V1-V5 and other flow control devices (e.g., check valves, louvers, flow restrictors, timing systems, etc.) can be used to control fluid flow through reactors 1 and 7 for the first, second, fourth, and fifth mixtures, and the optional purge gas when used. These mixtures are described further below. For example, a means for conveying fuel (via conduit 305) and oxidant (via conduit 3051) into the appropriate channels in the first reactor may include one or more of plenums, valves, vanes, spargers and/or distributors. Suitable spargers, distributors, etc., are disclosed in U.S. Pat. No. 7,815,873, which is incorporated by reference herein in its entirety. Although the present embodiments are compatible with the use of conventional spargers, distributors, plenums, etc., in stage 206, the invention is not limited thereto.

In this embodiment, the pyrolysis system utilizes valves (e.g., V1, V2, V3, V4, and V5) to manage the flow of streams through the reactor system as illustrated schematically in FIG. 1B. Referring to FIG. 1B, valves V1, V4, and V5 are open during the heating step and valves V2 and V3 are closed. The first reactant is conducted through conduit 305 to first distributor D1, which directs the flow of the first reactant into the first reactor 7, while the second reactant is conducted via conduit 3051 through the first reactor 7. The first and second reactants flow through reactor 7 via channels 14 and 16, respectively, which channels 10 to are comprised of sets of passages within the bed packing of the reactor 7. The reactants react in the mixing zone 13, then pass through the second reactor 1, and are conducted away from the reactor via conduit 2066. During the pyrolysis step, valves V1, V4, and V5 are closed and valves V2 and V3 are opened. The first mixture is conducted through conduit 2046, which provides the first mixture to the second reactor 1. The first mixture reacts within the first reactor 7 and in the mixing zone 13 and then passes through the first reactor 7 and is conducted away from the reactor via conduit 2065.

As a more specific example of the flow, the heating step begins by conducting first and second reactants to the first reactor 7. The first reactant is conducted to first reactor 7 via conduit 305. The second reactant is conducted to the first reactor by conduit 3051, which may optionally be substantially simultaneous with the conduction of the first reactant in conduit 305. In the embodiment illustrated in FIG. 1B, the first and second reactants do not mix appreciably upstream of end 11 of first reactor 7, e.g., ≥80.0% of the mixing of the first and second reactants by weight, such as ≥90.0%, occurs downstream of end 11 of first reactor 7. The invention is not limited to this embodiment, and this description is not meant to foreclose other embodiments within the broader scope of the invention, such as embodiments where there is a significant amount of fuel and oxidant mixing in the first reactor. Continuing with the embodiment illustrated in FIG. 1B, proximate to the downstream end 11 of the first reactor 7, the first and second reactants combine to produce a fourth mixture. The fuel and oxidant of the fourth mixture react exothermically at or proximate to a central region 13 of the reactor system. Optionally, the exothermic reaction continues downstream (with respect to the average flow of the fourth mixture) of region 13, e.g., in second reactor 1. The fifth mixture is conducted away from second reactor 1 via one or more conduits 2066. The heating step can result in a high temperature zone (also referred to by those skilled in the art as a temperature bubble), at least a portion of the temperature bubble being located in region 2063 (e.g., zones E, F, and/or G). The temperature bubble is illustrated schematically as a Gaussian-like shape in FIG. 1A.

The heating step thus includes the following features: (i) heating of region 13 and the second reactor 1 by transferring at least a portion of the heat of combustion to the reactor system downstream of the end 11 of the first reactor 7 and (ii) by transferring at least a portion of the sensible heat recovered by the first and second reactants in an upstream region of the first reactor (upstream with respect to the flow of the first and second reactants) toward one or more of the downstream region of the first reactor, region 13, or the second reactor to thermally regenerate the reactor system. Accordingly, at least a segment of each of the right-hand and left-hand edges the temperature profile translate downstream from their starting locations at the beginning of the heating step, as shown in FIG. 1A by arrows 6 and 8. It should be recognized that the translations indicated by arrows 2, 4, 6, and 8 of the temperature profile's edges during the heating and pyrolysis steps confines the temperature profile (which can achieve temperatures, e.g., >1600° C.) to regions of the reactor that can tolerate such conditions long term. Optionally, the shift in the edges of the temperature profile is accompanied by a shift in the position of the peak of the temperature profile. Operating conditions during the heating step can be substantially the same as those disclosed in U.S. Pat. No. 7,943,808. In an embodiment, the exothermic reaction of the fuel and oxidant components of the fourth mixture includes combustion, the combustion conditions including a temperature ≥1400° C., e.g., ≥1500° C., such as ≥1600° C., e.g., in the range of 1900° C. to 2200° C., and a pressure ≥1.0 bar (absolute), e.g., in the range of 1.0 bar to 15.0 bar, such as 2.0 bar to 8.0 bar.

Optionally, the heating step oxidizes ≥90.0 wt % of the first reactant's fuel component e.g., ≥99.0 wt %, based on the weight of the first reactant's fuel component. Optionally, diluent, such as nitrogen, that may be present in the fourth mixture is not oxidized to a significant extent. Optionally, ≥50.0% of the oxidation of the fourth mixture (based on the amount of the fourth mixture, mole basis, that is oxidized in region 2063), e.g., ≥75.0%, such as ≥90.0% of the oxidation occurs in the portion of region 2063 that is located between the first and second reactors.

In this embodiment, the total duration of generation step $t_2$ is for a time sufficient for the second reactor to abstract sufficient heat from the oxidation to accomplish the pyrolysis step. In other words, the heating step is conducted for a time duration greater than or equal to a time sufficient to displace the peak of the temperature toward the second reactor sufficient to heat the pyrolysis region 2064 for exposing the first mixture to a temperature ≥$1.20 \times 10^{3}$° C. during the pyrolysis step. Optionally, $t_2$ is in the range of 0.1 seconds to 30.0 seconds. Optionally, the total amount of heat added to the reactor system during the regeneration step does not exceed the sum of the heat that is required (a) to sustain the pyrolysis reaction for endothermically driving the second mixture from the pyrolysis portion of the first mixture and (b) for heat losses from the system, e.g., by as conduction losses through reactor walls and/or convective losses with, e.g., the second mixture. Optionally, the total amount of heat stored in the reactor system is generally much more than the minimum amount of heat needed for the pyrolysis step.

During the pyrolysis step (e.g., the reaction step), the second reactor 1 is at an elevated temperature and the first reactor 7 is at a lower temperature than the second reactor 1. A first mixture (e.g., a pyrolysis feed) is introduced via a conduit 2046, into a first end 3 of the second reactor 1. The first mixture abstracts heat from the reactor 1 and is reacted, optionally with a catalyst, to produce the desired pyrolysis reaction.

At least a portion of a second mixture derived from the first mixture exits the second reactor 1 through a second end 5 at an elevated temperature and passes through the first reactor 7, entering through a first end 11 and exiting at a second end 9. A vapor-phase portion of the second mixture is conducted away from the reactor system via conduit 2065, with a second portion of the second mixture optionally remaining in one or more of reactor 1 or 7 or mixing zone 13, e.g., as a deposit, such as a coke deposit. The first reactor 7 is initially at a lower temperature than the second reactor 1. As the first and/or second mixture pass through the first reactor 7, they are cooled to a temperature subsisting proximate to the second end 9 of first reactor 7. The temperature at that location can be, e.g., approximately the same temperature as that of the fuel and oxidant introduced at that location during the heating step (the regeneration step) of the cycle.

As an exemplary embodiment, the regenerative material (e.g., bed packing material) in first reactor 7 of FIG. 1A is divided into two zones of roughly equal length and volume. The first reactor 7 has a length of 0.51 meters (20 inches). The base zone encompasses the portion of the reactor that extends from end 9 to about halfway through the reactor. That is, the base zone includes a volume roughly comparable to zones A and B in FIG. 1A. The temperature in these zones range from about 325° C. to about 1125° C., which results in a zone temperature $T_B$ of about 735° C. The reactor bed within the base zone comprises 400 cpsi ($6.2 \times 10^5$ cells/m²) square-pattern honeycomb having a channel width of 1 millimeter (mm). Wetted area $a_{vb}$ of this base zone is 4D (cells/area)=2480 m⁻¹. The second (j=2) zone extends from the hot end of the base zone (e.g., edge of zone B) to end 11 of reactor 7. That is, the hot zone (e.g., a portion of the reactor zone) includes roughly a volume comparable to zones C and D in FIG. 1A. Temperature in this zone ranges from about 1250° C. to about 1615° C., and the zone temperature $T_2$ is 1450° C. Using the equation (e1), an X parameter value of X=0.5 gives a design target $R_{jb}$ of 0.192, and a corresponding $a_{v2}$ is 476 m⁻¹. The regenerative contents (e.g., bed packing material) of the second zone comprise 15 cpsi ($2.33 \times 10^4$ cells/m²) square-pattern honeycomb having a channel width of 5 mm. Wetted area $a_{v2}$ of this second zone is 465 m⁻¹. During the regeneration step, fuel and oxidant are flowed through first reactor 7 at a rate of 23,600 kghr⁻¹ m². Pressure drop in the first reactor 7, which may have been 1.73 pounds per square inch (psi) (11.9 kPa) had both zones of the reactor contained a 400 cpsi ($6.2 \times 10^5$ cells/m²) honeycomb, is reduced to 0.70 psi (4.8 kPa) with the second zone containing a 15 cpsi ($2.33 \times 10^4$ cells/m²) honeycomb.

As a second exemplary embodiment, the regenerative material (e.g., bed packing material) in second reactor 1 of FIG. 1A is divided into two zones of roughly equal length and volume. The second reactor 1 has a length of 0.71 meters (28 inches). The base zone encompasses the portion of the reactor that extends from end 3 to about halfway through the reactor. That is, the base zone includes a volume roughly comparable to zones G and H in FIG. 1A. The temperature in these zones range from about 250° C. to about 1050° C., which results in a zone temperature $T_B$ of about 645° C. The reactor bed within the base zone comprises 400 cpsi ($6.2 \times 10^5$ cells/m²) square-pattern honeycomb having a channel width of 1 mm. Wetted area $a_{vb}$ of this base zone is 2480 m⁻¹. The second (j=2) zone extends from the hot end of the base zone (e.g., edge of zone G) to end 5 of reactor 1. That is, the hot zone (e.g., a portion of the reactor zone) includes roughly a volume comparable to zones E and F in FIG. 1A. Temperature in this zone ranges from about 1120° C. to about 1760° C., and the zone temperature $T_2$ is 1460° C. Using the equation (e1), an X parameter value of X=0.5 gives a design target $R_{jb}$ of 0.153, and a corresponding $a_{v2}$ is 379 m⁻¹. The regenerative contents (e.g., second bed packing) of the second zone comprise 10 cpsi ($1.55 \times 10^4$ cells/m²) square-pattern honeycomb having a channel width of 6 mm (0.006 m). Wetted area $a_{v2}$ of this second zone is 372 m⁻¹. During the pyrolysis step, the first mixture is flowed into second reactor 1 at a rate of 10,400 kghr⁻¹ m⁻². Pressure drop in the second reactor 1, which would have been 3.31 psi (22.8 kPa) had both zones of the reactor contained 400 cpsi ($6.2 \times 10^5$ cells/m²) honeycomb, is reduced to 1.37 psi (9.4 kPa) with the second zone containing 10 cpsi ($1.55 \times 10^4$ cells/m²) honeycomb.

It should be noted that for differences in the wetted area ≤25%, it may not be necessary to adjust the wetted area, as the impact on the pressure-drop/efficiency tradeoff may be too small to take advantage by means of significant change to the reactor design. For example, if the 10 cpsi ($1.55 \times 10^4$ cells/m²) honeycomb of the second example above (wetted area 372 m⁻¹) had been deployed in the second zone (e.g., zones C and D) of the first reactor 7 in the first example above (instead of the 15 cpsi ($2.33 \times 10^4$ cells/m²) honeycomb having 465 m⁻¹ wetted area), the pressure drop may be reduced by approximately an additional 2% (from 4.84 kPa to 4.76 kPa). The use of available bed packing having an $a_v$ of 372 m⁻¹ may be acceptable, because the pressure-drop/efficiency tradeoff is dominated by the reduction from 2480 m⁻¹ to 372 m⁻¹, not by the (20%) difference between 465 m⁻¹ and 372 m⁻¹.

As a third exemplary embodiment, the reactor has a first reactor 7 that is arranged 10 to as described in the first example above (e.g., 15 cpsi ($2.33 \times 10^4$ cells/m²) in hot zone), and has a second reactor 1 that is arranged as described in the second example above (e.g., 10 cpsi ($1.55 \times 10^4$ cells/m²) in hot zone). The third exemplary embodiment refers to pressure drops through the assembly of both reactors 1 and 7. For this comparison, an all-400 cpsi ($6.2 \times 10^5$ cells/m²) reactor may be 1.22 meters (48 inches) as the base embodiment. For variations in the wetted areas (e.g., using different wetted areas) the enhanced embodiment has double the L/D. In this example, achieving double the L/D means that length is increased 60% and the diameter is decreased 20%. This change provides roughly the same bed volume and residence time at twice the L/D. Accordingly, the length is 1.6 times the length of the base embodiment (1.22 meters), which results in a length of 1.95 meters for the combined reactors 1 and 7 in the enhanced embodiment. The combined reactors may be divided in the same proportions as noted above.

During the regeneration step, fuel and oxidant of fourth mixture are flowed through first reactor 7 at a rate of 23,600 kghr⁻¹ m⁻². During the pyrolysis step, the first mixture is flowed into second reactor 1 at a rate of 10,400 kghr⁻¹ m⁻². If this reactor system had contained 400 cpsi ($6.2 \times 10^5$ cells/m²) honeycomb throughout the reactor, the pressure drop may have been 5.68 psi (39.2 kPa) during the regeneration step and 8.30 psi (57.3 kPa) during the pyrolysis step. In this third example, the use of lower wetted area in the hot zone enables the reactor to be designed with an L/D ratio that is double the L/D of the all-400 cpsi ($6.2 \times 10^5$ cells/m²) case, while maintaining comparable pressure drop of 4.32 psi (29.8 kPa) during the regeneration step and 7.66 psi (52.8 kPa) during the pyrolysis step. Thus, the use of the regions of reduced wetted areas enables the pyrolysis technology to be applied in a more cost-effective and better performing reactor, while maintaining the efficiency that results from having high heat transfer coefficients.

The invention is not limited to embodiments where the zones of different wetted areas in the first reactor 7 comprise two contiguous regions only. For example, in other embodiments, first reactor 7 comprises a honeycomb monolith in the form of an elongated polygonal body. The honeycomb comprises two or more portions, the portions being in side-to-side contact, with each section having, e.g., (i) one or more flow passages feeding into a flow passage in the adjacent portion. That is, the portions may be adjacent to each other (e.g., with each upstream of the mixing means or each downstream of the mixing means). For instance, the first reactor 7 may include (i) a reactor bed or bed packing material having three different portions disposed in series with three wetted areas, $a_{v1} \neq a_{v2}$, and $a_{v3}$ and (ii) having a to respective plurality of flow passages through the respective portions. These portions may correspond to a first portion as zones A and B, a second portion as zone C, and a third portion as zone D. The wetted areas may be such that $a_{v1} \neq a_{v2}$ and $a_{v2} \neq a_{v3}$ (e.g., each are different by at least 25%). That is, the ratio of $a_{v2}$ to $a_{v1} \leq 0.75$ and one of the ratio of $a_{v3}$ to $a_{v2} \leq 0.75$. In these embodiments, the first mixture and/or the second mixture flow through the passages between the portions, which may be different bed packing (e.g., monoliths adjacent to each other, different packed bed, and/or different tiles) along the flow path. Similarly, one of the portions may optionally have a mixing means (e.g., mixing components or a gap) disposed between the portions. The wetted areas may again be such that $a_{v1} \neq a_{v2}$ and $a_{v2} \neq a_{v3}$. However, for this example, the ratio of $a_{v2}$ to $a_{v1} \leq 0.75$, while the ratio of $a_{v3}$ to $a_{v2}$ may be in the range of 0.8 to 1.2 or may be in the ratio of $a_{v3}$ to $a_{v1}$ is in range of 0.8 to 1.2.

In other embodiments, the bed packing may include four or more portions within a reactor. These portions may be adjacent to each other (e.g., with each upstream of the mixing means or each downstream of the mixing means) or may optionally have a mixing means (e.g., mixing components or a gap) disposed between the portions. As an example, the wetted areas may be such that $a_{v1} \neq a_{v2}$ and $a_{v3} \neq a_{v4}$ (e.g., each are different by at least 25%). For each of the portions being disposed adjacent to each other, the ratio of $a_{v2}$ to $a_{v1} \leq 0.75$, the ratio of $a_{v3}$ to $a_{v2} \leq 0.75$, and the ratio of $a_{v4}$ to $a_v3 \leq 0.75$. For two portions being disposed adjacent to each other with a mixing means disposed between the other two portions, the ratio of $a_{v2}$ to $a_{v1} \leq 0.75$, the ratio of $a_{v3}$ to $a_{v4} \leq 0.75$, the ratio for $a_{v3}$ to $a_{v2}$ may be in range of 0.8 to 1.2, or the ratio for $a_{v1}$ to $a_{v4}$ may be in the range of 0.8 to 1.2.

As an example, the reactor bed or a portion of the reactor bed may be comprised of honeycomb monoliths. Monoliths that have straight channels may be utilized to minimize pressure drop and enable greater reactor length. Preferred honeycomb monoliths may have channel densities that range from about 1 cell/cm$^2$ to 250 cells/cm$^2$. Accordingly, if the reactor bed is a honeycomb monolith, the wetted area $a_{v1}$ may be in a range of 500 m$^{-1}$ to 4000 m$^{-1}$, wherein the second portion of the honeycomb monolith may have a wetted area $a_{v2}$ in the range of 100 m$^{-1}$ to 1000 m$^{-1}$. In other embodiments, the first wetted area $a_{v1}$ may be in a range of 800 m$^{-1}$ to 3000 m$^{-1}$, wherein the second portion of the honeycomb monolith may have a wetted area $a_{v2}$ in the range of 100 m$^{-1}$ to 800 m$^{-1}$.

In another embodiment, the first reactor 7 comprises a honeycomb monolith in the form of an elongated polygonal body having a first wetted area $a_{v1}$ and defines a first plurality of flow passages. The second reactor 1 comprises a honeycomb monolith in the form of an elongated polygonal body having a second wetted area $a_{v2}$ and defines a second plurality of flow passages. Either or both of reactors 1 and 7 may be divided into two or more zones having wetted areas may be such that $a_{v1} \neq a_{v2}$ (e.g., each are different by at least 25%). In these embodiments, the first mixture flows through the first plurality of flow passages and the second mixture flow through the second plurality of flow passages. These reactors may be adjacent to each other with the mixing means consisting essentially of a gap between the reactors 1 and 7 or one or more mixing components, which may include different plates and or baffles.

Further, the reactor beds may include various bed packing, which may have different wetted areas. That is, the bed packing may include one or more of monoliths, pebble beds, tiles and/or combinations of different bed packings. For instance, a monolith may be disposed adjacent to a pebble bed and/or other particulate packing, which may have a different wetted area.

In another embodiment, a foam monolith or packed bed may be utilized. These packings provide a more tortuous flow passage and have pore densities in the range of about 1 pore/cm to 20 pore/cm. In yet another embodiment, tiles may be utilized, which may have a wetted surface area in the range of 10 m$^{-1}$ to 500 m$^{-1}$. The first mixture, second mixture, third mixture, and fourth mixture will now be described in more detail.

Mixtures

In an embodiment, the first mixture comprises ≥10.0 wt % hydrocarbon based on the weight of the first mixture and optionally further comprises molecular hydrogen and/or diluent. The term "hydrocarbon" means (i) molecules (and mixtures thereof) including both carbon atoms and hydrogen atoms, and optionally including other atoms (heteroatoms) such as oxygen, sulfur, and nitrogen, wherein the carbon atoms and hydrogen atoms together comprise ≥75.0% of the atoms present in the molecule or mixture of molecules. The term "molecular hydrogen" means H$_2$. The type of hydrocarbon is not critical; e.g., the hydrocarbon can even compromise hydrocarbon non-volatiles, including those that are not in the gas phase at the temperature, pressure, and composition conditions subsisting at the inlet to the pyrolysis reactor.

In an embodiment, the hydrocarbon is derived from one or more source materials. The term "source materials" means sources, containers, conduits, vessels, reservoirs, etc., of hydrocarbon. Examples of source materials comprising hydrocarbon include one or more of methane, methane-containing streams, distillates, residues, hydrocarbon streams derived from plant or animal matter and/or combinations thereof. Suitable hydrocarbon source materials include those described in U.S. Pat. Nos. 7,943,808 and 7,544,852, which are incorporated by reference herein in their entirety.

The first mixture can be derived from the source material(s) located upstream of the pyrolysis, but this is not required. For example, in one embodiment hydrocarbon derived from a first source material and hydrogen derived from a second source material are conducted separately to the pyrolysis reactor, the hydrocarbon and hydrogen being combined to produce the first mixture proximate to (e.g., within) the pyrolysis reactor. Optionally, the hydrocarbon has (or is derived from one or more source materials having), e.g., a hydrogen content in the range of 6.0 wt % to 25.0 wt %, 8.0 wt % to 20.0 wt % (e.g., not natural gas), or 20.0 wt % to 25.0 wt % (e.g., natural gas). The term "hydrogen content" of a mixture or source material means atomic hydrogen bound to carbon and/or heteroatoms covalently bound thereto and which excludes molecular hydrogen (H$_2$) in the mixture (or source material) expressed as a weight percent based on the weight of the hydrocarbons in the mixture (or source material).

When the first mixture further comprises molecular hydrogen, the first mixture optionally has a molecular hydrogen to carbon (as all carbon atoms in the first mixture that are not bound to oxygen atoms, e.g., as can be determined by Nuclear Magnetic Resonance Spectroscopy) molar ratio in the range of from 0.0 to 15.0, e.g., 0.1 to 4.0, such as 1.0 to 3.0 or 1.0 to 2.0. Optionally, the first mixture has a hydrogen (all hydrogen atoms in the first mixture regardless of atomic or molecular form) to carbon (all carbon atoms in the first mixture regardless of atomic or molecular form) atomic ratio in the range of from 1.0 to 15.0, e.g., in the range of from 3.0 to 8.0.

Optionally, the first mixture further comprises diluent, e.g., $\geq 1.0$ wt % of diluent based on the weight of the first mixture. Suitable diluents (which can be a diluent mixture) include one or more of oxygenate, nitrogen ($N_2$), hydrogen sulfide, $C_{4+}$ mercaptans, amines, mixtures of amines, non-hydrocarbon non-volatiles (whether combustible or not) including refractory inorganics such as refractory oxygenates, inert gas (including inert gas mixtures), etc. In an embodiment, the first mixture comprises $\leq 10.0$ wt % diluent. The term "non-volatiles" means molecules and mixtures thereof having a nominal atmospheric boiling point $\geq 570.0°$ C., e.g., refractory oxygenates, refractory hydrocarbons, metals, minerals, etc. American Society of Testing and Materials ("ASTM") methods can be used to determine the nominal atmospheric boiling point (ASTM Method 1078) and the amount and properties of such non-volatiles, such as ASTM Methods D-6560, D-7061, D-189, D-482, D-524, and D-2415. Non-volatiles that are capable of being combusted are called "combustible non-volatiles". The term non-volatiles encompasses e.g., coke, ash, soot, resid, metal, mineral, ash-forming asphaltenic, tar, etc., including those formed, e.g., during or after oxidation (e.g., combustion or partial oxidation) and/or pyrolysis, including those which may remain as a residue or deposit in the reaction zone. Optionally, one or more mixtures and/or source materials comprises $C_{3+}$. The term "$C_{3+}$" means molecules having at least three carbon atoms, including, e.g., coke and soot, whether those products emerge from the reactor or remain within the pyrolysis reactor. The term coke means combustible non-volatile products of pyrolysis that remain in the reactor, while the term soot means combustible non-volatile products of pyrolysis that are carried out of the reactor (e.g., in the reactor effluent). The term "reactor effluent" means products of pyrolysis conducted away from the reactor. The reactor effluent comprises $C_2$ unsaturates, where the term "$C_2$ unsaturates" means hydrocarbon having two carbon atoms and $\leq 4$ hydrogen atoms.

In an embodiment, the second mixture comprises $\geq 1.0$ wt % of $C_2$ unsaturates and $\geq 1.0$ wt % of combustible non-volatiles, based on the weight of the second mixture. Optionally, $\geq 50.0$ wt %, e.g., $\geq 75.0$ wt %, such as $\geq 90.0$ wt % of the combustive non-volatiles comprise $C_{3+}$ species such as coke, based on the weight of the combustible non-volatiles in the second mixture. For example, the second mixture can comprise an amount $ac_1$ of $C_2$ unsaturates and an amount $ac_2$ of $C_{3+}$ hydrocarbon, wherein (i) $ac_1 \geq 1.0$ wt % and $ac_2 \geq 0.1$ wt % based on the weight of the second mixture and (ii) the $C_{3+}$ hydrocarbon comprises $\geq 90$ wt % coke based on the weight of the $C_{3+}$ hydrocarbon in the second mixture. Optionally, the second mixture further comprises one or more of hydrogen, methane, ethane, or diluent. Besides coke, the $C_{3+}$ hydrocarbon optionally further comprises benzene, paraffin (iso-, cyclo-, and/or normal) having $\geq 3$ carbon atoms, etc. Optionally, the second mixture has an $ac_2:ac_1$ ratio $\leq$ about 1.0, e.g., $\leq$ about 0.6, such as $\leq$ about 0.4. Optionally, the second mixture has one or more of the following additional properties: an acetylene:ethylene molar ratio in the range of about 0.5 to about 20.0, e.g., about 1.0 to about 10.0, such as about 1.5 to about 6.0; a molecular hydrogen:$C_2$ unsaturates molar ratio in the range of 2.0 to 20.0; a molecular hydrogen:acetylene molar ratio $\geq 0.75$, or $\geq 3.0$, e.g., in the range of 3.0 to 20.0. Optionally, the second mixture comprises $\geq 1.0$ wt %, methane e.g., 2.0 wt % to 50.0 wt %; $\geq 1.0$ wt % molecular hydrogen, e.g., 2.0 wt % to 5.0 wt %; $\geq 1.0$ wt % acetylene, e.g., 2.0 wt % to 40.0 wt %; $\geq 1.0$ wt % ethylene, e.g., 2.0 wt % to 70.0 wt %, such as 2.0 wt % to 20.0 wt %; and $\geq 1.0$ wt % $C_{3+}$, e.g., 2.0 wt % to 50.0 wt %, the weight percents being based on the weight of the second mixture.

In an embodiment, $\geq 90$ wt % of the second mixture's combustible non-volatiles remain in the regenerative, reverse-flow pyrolysis reactor, e.g., as a deposit in the passages of the first and/or second reactor, the weight percents being based on the weight of the combustible non-volatiles in the second mixture.

Producing the second mixture from the first mixture by pyrolysis is an endothermic reaction, which withdraws heat from the pyrolysis reactor system. At least a portion of this heat can be replaced, e.g., during a regeneration step, so that the process can be operated in sequence (pyrolysis step followed by regeneration step), e.g., continuously.

The fourth mixture comprises first and second reactants, e.g., fuel and oxidant. Exothermically reacting the fuel and oxidant provides at least a portion of the heat utilized by the pyrolysis, e.g., $\geq 50\%$, such as $\geq 75\%$, or $\geq 95\%$ of the heat utilized by the pyrolysis. Additional heat, when needed, can be provided to the regenerative, reverse-flow pyrolysis reactor by, e.g., a burner or furnace, e.g., a furnace external to the reactor, but in thermal communication therewith. The fuel and oxidant mix within the mixing zone 13 to produce the fourth mixture, the fuel and oxidant then reacting, e.g., by an oxidation reaction, such as combustion. The fuel can comprise, e.g., molecular hydrogen, synthesis gas (mixtures of CO and $H_2$), or hydrocarbon, such as $\geq 10.0$ wt % hydrocarbon (including mixtures thereof), or $\geq 50.0$ wt % hydrocarbon, or $\geq 90.0$ wt % hydrocarbon based on the weight of the fuel. The oxidant can comprise, e.g., $\geq 10.0$ wt % molecular oxygen, e.g., $\geq 50.0$ wt % molecular oxygen, or $\geq 90.0$ wt % molecular oxygen based on the weight of the oxidant. When the fuel comprises hydrocarbon, the particular hydrocarbon selected is not critical. For example, in an embodiment, the hydrocarbon comprises one or more of the hydrocarbons specified for the first mixture, e.g., methane. In an embodiment, the hydrocarbon is derived from, comprises, consists essentially of or consists of one or more of methane, methane containing streams such as coal bed methane, biogas, associated gas, natural gas and mixtures or components thereof, etc. When the fuel comprises hydrogen and/or hydrocarbon, the choice of oxidant is not critical, provided the oxidant is capable of exothermically reacting with the hydrogen and/or hydrocarbon. For example, in an embodiment, the oxidant comprises, e.g., molecular oxygen and/or ozone.

It is generally beneficial to increase the amount of oxidant in the fourth mixture beyond that needed to oxidize substantially all of the fourth mixture's fuel, e.g., to oxidize combustible non-volatiles remaining in the reactor beds as a result of the pyrolysis of the first mixture.

Optionally, the fourth mixture further comprises diluent, e.g., $\geq 1.0$ wt % of diluent based on the weight of the first mixture. Suitable diluents (which can be a diluent mixture) include one or more of, e.g., oxygenate (water, carbon dioxide, etc.), non-combustible species, nitrogen ($N_2$), hydrogen sulfide, $C_{4+}$ mercaptans, amines, mixtures of amines, non-hydrocarbon non-volatiles (whether combustible or not) including refractory inorganics such as refractory oxygenates, inert gas (including inert gas mixtures), etc. In an embodiment, the fourth mixture comprises $\leq 96.0$ wt % diluent, e.g., in the range of 50.0 wt % to 95.0 wt % diluent, based on the weight of the fourth mixture.

In an embodiment, the fourth mixture comprises ≥1.0 wt % molecular oxygen, e.g., in the range of 5.0 wt % to 25.0 wt %, such as 7.0 wt % to 15.0 wt %; ≥0.1 wt % fuel, e.g., in the range of 0.5 wt % to 10.0 wt %, such as 1.0 wt % to 5.0 wt %, the weight percents being based on the weight of the fourth mixture, with the balance of the fourth mixture being diluent.

The fifth mixture comprises (i) products derived from the exothermic reaction of the fourth mixture's fuel and oxidant, and optionally (ii) diluent, when diluent is present in the fourth mixture, (iii) unreacted fuel and oxidant, and/or (iv) products derived from the reaction of the fourth mixture with combustible, non-volatiles in the reactor. When the exothermic reaction of the fuel and oxidant involves hydrocarbon combustion, or when a diluent is present in the fourth mixture (such as $N_2$ or $H_2S$), the fifth mixture can comprise carbon oxides, and can further comprise sulfur oxides, nitrogen oxides, etc.

A continuous or semi-continuous process for deriving (a) the second mixture from the first mixture and (b) the fifth mixture from the fourth mixture in a regenerative, reverse-flow reactor system will now be described in more detail. One feature of this process is the use of mixing means in zone 13, which is located between reactor 7 and reactor 1.

Reactor Components—Process Flow Components

In an embodiment, the reactor has various reactor components (e.g., process flow components, which are reactor beds that include one or more variants of bed packing material) that are utilized within the reactor system. Different wetted areas may be preferred for different zones within a reactor based on the conditions for that location and the intended use at that location. The process flow components may include components that manage the flow of process fluids (e.g., first mixture, second mixture, fourth mixture and fifth mixture) through the zones within the reactor. As an example, the process flow components may include mixing-distributor means, reactor beds, inlet and/or outlet means (e.g., valves and/or spargers), conduits and the like. The insulation components may include components that provide inhibit the transfer of heat from the interior of the reactor to locations external to the reactor, which may also inhibit the flow of process fluids (e.g., first mixture, second mixture, fourth mixture, and fifth mixture) to locations external to the reactor. Optionally, the materials that the reactor components are formed from maintain integrity, functionality, and withstand long term exposure to temperatures ≥1200° C., preferably ≥1500° C., more preferably ≥1700° C., and even more preferably ≥2000° C. for operating margin.

The reactor components may be exposed to different temperatures, as noted in FIG. 1A, which may involve different properties based on the function and location within the reactor. That is, the different reactor components may experience different temperatures, as noted in FIG. 1A. For instance, at the ends of the reactor, the reactor components may be exposed to temperatures below 900° C., while reactor components in zones B, C, D, E, F and/or G (e.g., in portions of the reactor beds and mixing zone) may be exposed to temperatures greater than 900° C. and may even be in excess of 2000° C. for certain portions of the reactor.

Because of the temperature profile, certain thermally related properties may be utilized for process flow components based on the location within the reactor. Examples of these properties include thermal capacity, heat transfer (e.g., emissivity, thermal conductivity) and temperature stability. Of these properties, the heat transfer properties provide certain flexibility to enhance the operation of the conversion process, while the thermal capacity and temperature stability are discussed further below. Each of these heat transfer properties may vary for different components, such as between process flow components and insulation components or between process flow components.

The heat transfer to the fluids in the stream at a location within the reactor is based on conduction, convection, radiation and/or chemical reaction. Accordingly, the reactor components may be configured to facilitate efficient heat transfer rates at various locations within the reactor based on the heat transfer mechanism that dominates that location. That is, convection and conduction properties may influence the heat transfer rate as compared to radiant properties for portions of the reactor that are exposed to temperatures below 700° C., for example. Accordingly, these portions of the reactor may include more wetted area for transfer of heat to the stream passing through the process flow components. In other portions of the reactor, radiant heat transfer properties tend to dominate the heat transfer as compared with convection and conduction properties.

Accordingly, flow components in certain zones of the reactor may be formed from the above mentioned materials, but others may involve other materials, such as yttria. Yttria-based refractory material provides high refractoriness having a pyrometric cone equivalent of >1600° C. Yttria is non-volatile in reducing atmospheres and chemically inert in carburizing environments. High-yttria refractory material contains yttria (e.g., $Y_2O_3$) greater than (>) 50 wt %, >70 wt %, >90 wt %, or >95 wt % of the total weight of the refractory component. Various raw materials can be used to manufacture high-yttria refractory products, which include sintered yttria, fused yttria grogs, chemically synthesized yttria powder, spray-dried, and calcined granules.

The properties, such as formability, strength, grain size and distribution, chemical inertness, thermal capacity and temperature stability, may also be adjusted for these process flow components at different locations. Examples of these properties and associated materials utilized in the reactor components are described in various applications, such as U.S. Pat. Nos. 7,815,873 and 7,846,401; along with U.S. Patent Application Publication Nos. 2007/0191664; 2009/0008292; 2008/0300438; 2009/0250377; 2010/0126907; 2010/0130803; 2010/0292522; 2010/0290978; 2010/0288617; 2010/0292523; and 2011/0011768, which are each incorporated by reference herein. Other materials may be utilized in portions of the reactor that are not subjected to operating conditions (e.g., environment or temperatures) that are problematic.

As an exemplary embodiment, a portion of the reactor (e.g., reactor bed or process flow components) may be formed from specific materials. For instance, one or both of the first portion and the second portion of the reactor bed may comprise yttria $(Y_2O_3) \geq 50$ wt % of the total weight of the respective portion of the reactor bed. In another embodiment, one or both of the first portion and the second portion of the reactor bed comprises from 0.001 wt % to 5 wt % of compounds that comprise elements selected from the group consisting of Al, Si, Mg, Ca, Fe, Mn, Ni, Co, Cr, Ti, Hf, V, Nb, Ta, Mo, W, Sc, La, and Ce, and mixtures thereof based upon the weight of the respective portion of the reactor bed.

Operation in a Regenerative, Reverse-Flow Thermal Pyrolysis Reactor

In one or more embodiments, various reactors and methods may be utilized. For instance, the reactors and methods may include those described in patent applications, such as U.S. Pat. No. 7,815,873 and U.S. Patent Application Publication Nos. 2007/0191664; 2009/0008292; 2008/0300438; 2010/0126907; and 2010/0130803, which are each incorporated herein by reference. These patent and patent applications teach and disclose various apparatus and methods for pyrolyzing hydrocarbon feeds in reverse flow regenerative pyrolysis reactors, including deferred combustion and controlled heat positioning processes.

Figure 2:
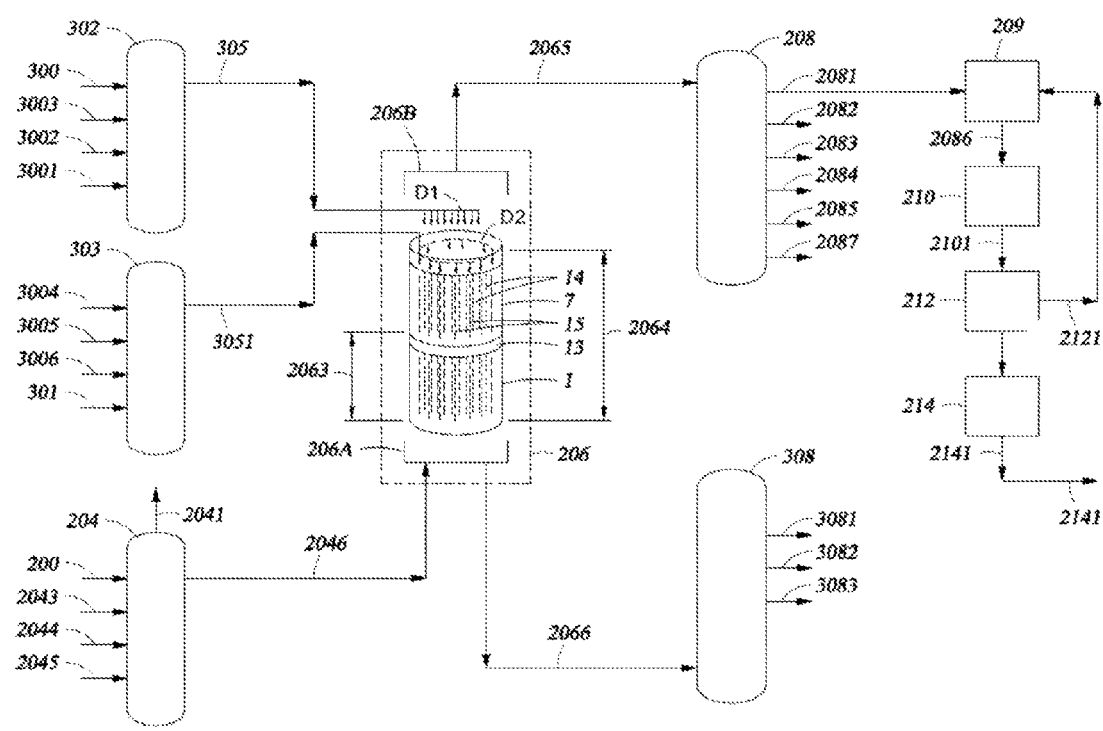
FIG. 2 schematically illustrates an exemplary configuration of a pyrolysis process utilizing a pyrolysis reactor in accordance with an embodiment of the present invention.

Referring now to FIG. 2, the process comprises regeneration and pyrolysis steps carried out in pyrolysis stage 206, wherein stage 206 utilizes the regenerative, reverse-flow thermal pyrolysis reactor illustrated schematically in FIGS. 1A and 1B. As shown in the figures, stage 206 comprises two reactors: a first (recuperator/quenching) reactor 7 and a second (pyrolysis) reactor 1, the first reactor 7 comprising at least one first channel 14 and at least one second channel 15. In the embodiment of FIG. 1B, the exothermic reaction zone 2063 can be located, e.g., between a first point proximate to the downstream end 11 of first reactor 7 and a second point proximate to the downstream end 3 of second reactor 1; "downstream" in this case being with respect to the average flow of the fourth mixture. The pyrolysis zone 2064 can be located, e.g., between a first point proximate to the upstream end 3 of the second reactor 1 and a second point proximate to the downstream end 9 of first reactor 7, "upstream" and "downstream" now being with respect to the average flow of the first mixture. It should be appreciated that the embodiments can be practiced without precisely defining (a) the boundaries of zones 2063 and 2064. Although zone 2063 (the exothermic reaction zone) is at least partially coextensive with pyrolysis zone 2064, the upstream end of zone 2063 ("upstream" with respect to the average flow of the fourth mixture) is generally proximate to the location where sufficient fuel and oxidant combine to produce an exothermic reaction. The downstream (with respect to the average flow of the first mixture) end of zone 2063 is generally proximate to the downstream end of second reactor 1 as shown in FIG. 1B, though this is not required, and in at least one embodiment the downstream end of zone 2063 is located further downstream, e.g., in conduit 2066. In at least one of the embodiments represented by FIG. 1B, the upstream end of pyrolysis zone 2064 is proximate to the upstream end 3 of the second reactor 1. The downstream end of pyrolysis zone 2064 is proximate to the downstream end 9 of the first reactor 7. Because the quenching heats the first reactor 7, the regeneration step optionally includes cooling the first reactor, e.g., to shift the tail of the temperature profile (indicated by trend-line 8) away from end 9 of the first reactor 7, as illustrated schematically in FIG. 1B.

It is understood that flow control means (e.g., one or more of valves, rotating reactor beds, check valves, louvers, flow restrictors, timing systems, etc.) can be used to control gas flow, actuation, timing, and to alternate physical beds between the flow systems for the first, second, fourth, and fifth mixtures, and the optional purge gas when used. For example, stage 206 can further comprise means for conveying fuel (via conduit 305) and oxidant (via conduit 3051) into the appropriate channels in the first reactor. Such means can include, e.g., one or more of plenums, valves, vanes, spargers and/or distributors. Suitable spargers, distributors, which are disclosed in U.S. Pat. No. 7,815,873 and incorporated by reference herein in its entirety. Representative process flow components and/or insulation components may include any suitable combination of properties and/or compositions as described above.

During the pyrolysis step, the first mixture is conducted to the first zone (the pyrolysis zone) 2064 of the regenerative, reverse-flow pyrolysis reactor via at least one conduit 2046. The second mixture, derived from the first mixture by the pyrolysis is conducted away from zone 2064 via at least one conduit 2065. The reactor optionally includes means for directing the first mixture from conduit 2046 into the channels of the second reactor 1, e.g., plenum 206A and means (such as plenum 206B) for directing at least a portion of the second mixture, e.g., the portion in the vapor phase, to conduit 2065.

In the illustrative embodiment, zones 2063 and 2064 are at least partially coextensive as shown in FIG. 2. Zone 2063 encompasses at least the second reactor. Zone 2064 encompasses at least a portion of each of the first and second reactors. At least a portion of the heat produced in zone 2063 during the exothermic reaction of the fourth mixture during the regeneration step is used to provide at least a portion of the heat utilized in zone 2064 for the endothermic pyrolysis step. Optionally, a major amount (e.g., >50%) of the heat abstraction occurs in the portion of zone 2064 that is coextensive with zone 2063.

If desired, at least a portion of the second mixture's acetylene can be converted to ethylene. For example, a third mixture can be derived from at least a portion of the second mixture in optional upgrading stage 208, with the third mixture being conducted via at least one conduit 2086 to a conversion stage 210, for converting at least a portion of the third mixture's acetylene to a first product comprising ethylene.

In one embodiment, stage 208 includes upgrading means, e.g., means for removing from the second mixture one or more of hydrocarbon (such as saturated hydrocarbon and/or those containing one or more heteroatoms), diluent, non-volatiles, and hydrogen, etc. For example, stage 208 can include one or more of a tar and/or solid removal means, compression means, adsorption means, distillation means, washing means, or drying means. While stage 208 can encompass conventional processing, e.g., conventional separation means, the present invention is not limited thereto. Separation means can be used, e.g., for removing condensable species (e.g., condensable hydrocarbon) from the second mixture. Such condensable species may include vaporized liquids that condense, such as benzene, or those that can be separated via, e.g., cooled separations for example, adsorption, vapor liquid separators, flash drums etc. Suitable separations means include conventional distillation or refrigerated distillation means such as one or more of demethanators and $C_2$ splitters, etc., but the present invention is not limited thereto. The present techniques are compatible with low-pressure demethanizers and high-pressure demethanizers (e.g., those operating at a pressure ≥3.5 MPa). Stage 208 can include contacting the second mixture or a portion thereof with a fluid having a pH>7.0.

In an embodiment, at least a portion of any light-gas in the second mixture (e.g., one or more of hydrogen, light saturated hydrocarbon, such as methane, carbon dioxide, hydrogen sulfide, etc.) is removed in stage 208. Suitable light-gas removal means include one or more of separation, basic wash (e.g., caustic wash or amine scrubbing), etc. Optionally, the separation means includes one or more of pressure swing absorption, membranes and/or cryogenic distillation, electro-chemical separation, or liquid absorption. Light-gas separation means may be used to separate hydrogen, carbon monoxide, methane, nitrogen or other light gases. Optionally, the removed light gas can be used, e.g., to adjust the stoichiometry of the first or fourth mixtures (e.g., by increasing the hydrogen and/or diluent content, etc.), as a stripping medium (e.g., for upgrading one or more sources from which the first mixture is derived, such as by stripping upstream of stage 206, e.g., in stage 204), etc. For example, should the second mixture contain more hydrogen than is needed for acetylene conversion, at least a portion of the hydrogen in the second mixture can be removed, e.g., by partially cooling the second mixture (optionally at essentially constant pressure) to condense at least a portion of the second mixture and then separating therefrom a vapor comprising hydrogen. The separated hydrogen can be conducted away, e.g., for recycle to produce the first or fourth mixtures.

Optionally, stage 208 includes means for removing at least a portion of any water present in the second mixture, e.g., by one or more of a methanol treatment, such as those described in Belgian Patent No. 722,895, adsorption, extraction by diethylene glycol, etc. For example, stage 208 can include one or more driers located, e.g., downstream of caustic treatment, for removing at least a portion of the water, including conventional driers, e.g., molecular sieve dryers.

Stage 208 can include, e.g., means for cooling and then compressing the second mixture conducted away from stage 206. For example, in embodiments where stage 206 has an outlet pressure <the inlet pressure of the converter of stage 210, stage 208 can include, e.g., compressing at least the portion of the second mixture from which the third mixture is derived in order to achieve the desired stage 210 inlet pressure. Should the second mixture comprise acid gases (e.g., $CO_2$ and/or $H_2S$), these can be removed, for example, downstream of the compression—a desirable location because the gas volume has been reduced significantly during compression. Conventional methods are suitable for removing acid gases, e.g., caustic treatment, but the present invention is not limited thereto. Acid gases separated from the second mixture can be conducted away, e.g., for storage or further processing such as in a Claus plant.

In an embodiment, at least a portion of the hydrogen, saturated hydrocarbon, diluent, etc., separated from $C_2$ unsaturates in upgrading stage 208 is recycled, e.g., by combining such separated species with one or more of the first mixture's source materials, e.g., in preparation stage 204.

Optionally, the first product is conducted away from conversion stage 210 via conduit 2101 to stage 212 containing dividing means (e.g., a splitter). The dividing means convey a second portion of the first product away from a first portion. The second portion, which comprises, e.g., ethylene, saturated hydrocarbon, and hydrogen, is conducted to stage 209 via conduit 2121. Stage 209 comprise means for combining the second portion of the first product with the portion of the second mixture conducted away from stage 208 via conduit 2081, e.g., valve means, to produce the third mixture. The pyrolysis is now described in more detail.

Although the present invention is not limited thereto, conventional pyrolysis reactors can be adapted for use in stage 206. Suitable reactors include, for example, regenerative reverse flow reactors as described in U.S. Patent Application Publication No. 2007/0191664 and thermal pyrolysis reactors as described in U.S. Pat. No. 7,491,250; U.S. Patent Application Ser. No. 61/349,464; and U.S. Patent Application Publication Nos. 2007/0144940 and 2008/0142409, all of which are incorporated by reference herein in their entirety. In an embodiment, the thermal pyrolysis is conducted under high-severity thermal pyrolysis conditions, e.g., by exposing the first mixture to temperature in the range of about 1400° C. to about 2300° C., e.g., in the range of about 1450° C. to about 1800° C. Optionally, ≥25.0 wt % (such as ≥50.0 wt % or ≥75.0 wt %) of the first mixture achieves a peak pyrolysis gas temperature ≥1400° C., e.g., in the range of about 1500° C. to about 1675° C., based on the weight of the first mixture. The term "peak pyrolysis gas temperature" means the maximum temperature achieved by the bulk pyrolysis stream gases as they travel through the pyrolysis reactor (e.g., cracking zone or radiant zone). One skilled in the art will appreciate that temperatures immediately proximate to a partition may be higher, and may, in some infinitesimal boundary layer, actually approach the solid temperature. However, the pyrolysis temperature referred to herein should be considered a bulk gas temperature, which is a temperature that could be measured by a device (such as a thermocouple) that is not in contact with the solid material. For example, if the gas is traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

Although the process is robust and can operate within a wide range of pyrolysis conditions, e.g., temperature, pressure, residence times, severity, etc., the conditions are generally selected to increase the relative amount of $C_2$ unsaturates in the second mixture, e.g., to increase the acetylene to $C_{3+}$ weight ratio. Relatively long residence times can result in over-cracking of the feed molecules, leading to an undesirable increase in the amount of methane and/or $C_{3+}$ in the second mixture. In an embodiment, residence time is ≤about 0.3 seconds, e.g., ≤0.05 seconds. In an embodiment, the pyrolysis is high-severity, thermal pyrolysis and the residence time is ≤0.05 seconds, such as ≤0.02 seconds. Residence time can be selected, e.g., for optimum $C_2$ unsaturates' yield under pyrolysis conditions. This can be done by measuring the amount of $C_2$ unsaturates in the second mixture under substantially constant thermal pyrolysis conditions at a plurality of residence times. The optimum residence time can be approximated using conventional interpolation and extrapolation of the measured values. The optimum residence time can also be approximated using pyrolysis reaction simulations of second mixture composition as a function of pyrolysis conditions and residence time, including conventional pyrolysis reaction simulations.

In an embodiment, ≥90 wt % of the second mixture's combustible non-volatiles remain in the regenerative, reverse-flow pyrolysis reactor as a deposit in the at least some of the channels first and second of the first reactor, the weight percents being based on the weight of the combustible non-volatiles in the second mixture. The regeneration step can lessen the accumulation of such deposits.

In an embodiment, the pyrolysis is conducted for a time duration ($t_1$) sufficient for exposing ≥50.0 wt %, e.g., ≥75.0 wt %, such as ≥90.0 wt % of the first mixture (based on the weight of the first mixture) to pyrolysis conditions for a residence time ≤about 0.3 seconds, e.g., ≤0.05 seconds. In an embodiment, $t_1$ is ≤20.0 seconds, e.g., ≤10.0 seconds, such as ≤5.0 seconds. Optionally, $t_1$ is in the range of 1.0 seconds to 20.0 seconds.

In an embodiment, the pyrolysis step includes one or more of the following conditions: the first mixture achieves a peak pyrolysis gas temperature ≥1400° C., e.g., in the range of 1450° C. to 2200° C., such as, 1500° C. to 1900° C., or 1600° C. to 1700° C.; a total pressure ≥1.0 bar (absolute), e.g., in the range of 1.0 bar to about 15 bar, such as in the range of 2.0 bar to 10.0 bar; a high-severity residence time ≤0.1 seconds, e.g., ≤0.05 seconds, such as ≤0.005 seconds and/or a $t_1$ in the range of 1.0 seconds to 20.0 seconds. Optionally, the first mixture comprises ≥0.01 mole % of hydrocarbon, e.g., 0.1 mole % to 90.0 mole % of hydrocarbon and ≥0.01 mole % of molecular hydrogen, e.g., 0.1 mole % to 90.0 mole % of molecular hydrogen, the mole percents being based on the sum of the number of moles of hydrocarbon and hydrogen in one mole of the first mixture. At the conclusion of the pyrolysis step, optional upgrading stage 208 can be used, e.g., to separate from the second mixture species that may be useful in other stages of the process, e.g., via conduits 2082. The portion of the second mixture that is not used in other stages of the process can be conducted away from the process via one or more conduits 2087 for storage or further processing. Conventional separations processes are useful for stage 208, though the present invention is not limited thereto.

During the regeneration step, the fuel is conducted through at least one conduit 305 and optionally to at least one first distributor (D1), wherein D1 directs the flow of the fuel into first channels 14 within first reactor 7. The oxidant is conducted through at least one conduit 3051 and optionally to at least one second distributor (D2), wherein D2 directs the flow of the oxidant to second channels 15 within first reactor 7. The fuel and oxidant are combined in mixing zone 13 to produce the fourth mixture (for the exothermic reaction) in proximity to the downstream end of first reactor 7, which in this embodiment defines the upstream end of an exothermic reaction zone 2063. For the description of the regeneration step, upstream and downstream are defined with respect to the average flow of the fourth mixture, and components and products thereof. A fifth mixture, comprising at least a portion of the compositions resulting from the reaction of the fourth mixture's fuel and oxidant (and optionally including a portion of the fourth mixture that is not consumed in the reaction), is directed by plenum 206A to at least one conduit (2066), and conducted away from the regenerative, reverse-flow pyrolysis reactor. Optionally, oxidant conducted through channel(s) 15 during the regeneration step reacts with the combustible non-volatiles deposited therein during preceding pyrolysis steps, thereby lessening the amount of accumulated combustible non-volatiles.

In this embodiment, the total duration of a regeneration step $t_2$ is for a time sufficient for the second reactor to abstract sufficient heat from the oxidation to accomplish the pyrolysis step. In other words, the regeneration step is conducted for a time duration greater than or equal to a time sufficient to displace the peak of the temperature profile toward the second reactor sufficient to heat the pyrolysis zone 2064 for exposing the first mixture to a temperature $\geq 1200°$ C. during the pyrolysis step. The value of $t_2$ depends on factors, such as the geometry of the reactors utilized in stage 206, the heat transfer characteristics of the reactors and the materials from which the reactors are made, and the amount of heat needed by the pyrolysis step. Optionally, the $t_2$ is in the range of 1.0 seconds to 20.0 seconds. Optionally, the total amount of heat added to the reactor system during the regeneration step does not exceed the sum of the heats that are required (a) to sustain the pyrolysis reaction for endothermically driving the second mixture from the pyrolysis portion of the first mixture and (b) for heat losses from the system, e.g., by as conduction losses through reactor walls and/or convective losses with, e.g., the second mixture. Optionally, the total amount of heat stored in the reactor system though is generally much more than the minimum amount of heat needed for the pyrolysis step. In an embodiment, $t_2$ is greater than or equal to a time sufficient for heating the pyrolysis zone 2063 for exposing $\geq 50.0$ wt % of the first mixture, e.g., $\geq 75.0$ wt %, such as $\geq 90.0$ wt % to a temperature $\geq 1200°$ C. during the pyrolysis step; the weight percents being based on the weight of the first mixture. In an embodiment, $t_2$ is $\leq 20.0$ seconds, e.g., $\leq 10.0$ seconds, such as $\leq 5.0$ seconds.

In an embodiment, the exothermic reaction of the fuel and oxidant components of the fourth mixture includes combustion, the combustion conditions including a temperature $\geq 1400°$ C., e.g., $\geq 1500°$ C. such as $\geq 1600°$ C., e.g., in the range of $1600°$ C. to $2000°$ C., and a pressure $\geq 1.0$ bar (absolute), e.g., in the range of 1.0 bar to 15.0 bar, such as 2.0 bar to 5.0 bar.

Optionally, the regeneration step completely oxidizes the oxidizable species in the fuel, including hydrocarbon, hydrogen, etc. therein. Optionally, diluent such as nitrogen that may be present in the fourth mixture is not oxidized to a significant extent. Optionally, $\geq 50.0\%$ of the oxidation of the fourth mixture (based on the amount of the fourth mixture, mole basis, that is oxidized in zone 2063), e.g., $\geq 75.0\%$, such as $\geq 90.0\%$ of the oxidation occurs in the portion of zone 2063 that is located between the first and second reactors, e.g., in zone 13.

After at least a portion of the fifth mixture is conducted away from zone 2063, the first mixture is again conducted to zone 2064, and the process repeats in sequence—exothermically reacting the fuel and oxidant of the fourth mixture to heat the reactor and then utilizing at least a portion of the heat for pyrolyzing the first mixture. At the conclusion of the regeneration step, optional upgrading stage 308 can be used, e.g., to separate from the fifth mixture species that may be useful in other stages of the process, e.g., via conduits 3081-3083 as discussed, e.g., diluent can be separated from the fifth mixture and utilized to produce the fourth mixture. Conventional separations processes are useful for stage 308, though the present invention is not limited thereto.

The process can be operated sequentially, e.g., continuously, semi-continuously, or even in batch mode. In an embodiment, stage 206 comprises a plurality of pyrolysis reactors operating, e.g., in series, parallel, or a combination thereof, with at least one pyrolysis reactor having (i) pyrolysis step(s) and (ii) regeneration step(s) having the described first and second intervals. When stage 206 comprises a plurality of pyrolysis reactors, the sequence of regeneration steps and pyrolysis steps in each reactor can be out of phase, e.g., to provide a continuous flow of second mixture from the process. For example, the second mixture can be obtained from a first reactor in stage 206 undergoing a pyrolysis step while a second reactor is undergoing a regeneration step in a first period, and then in a second period the second mixture is obtained from the second reactor undergoing a pyrolysis step while the first reactor is undergoing a regeneration step.

Optionally, the process further includes one or more of the following components: treating/upgrading stage 308 for treating and/or upgrading the fifth mixture downstream of conduit 2066; one or more conduits for adding to the fourth mixture's fuel source material 300 one or more of molecular hydrogen and/or light saturated hydrocarbon, such as methane 3001 or diluent, such as oxygenate 3002; conduits for adding to the fourth mixture's oxidant source material 301 additional or supplemental oxidant 3003 or diluent 3004; one or more conduits for adding to the first source material one or more of molecular hydrogen 2043, hydrocarbon, e.g., light saturated hydrocarbon, such as methane 2044, or diluent, such as oxygenate 2045; one or more conduits for conducting away heteroatom species, such as hydrogen sulfide or non-volatiles 2041; one or more conduits for conducting away a first byproduct from upgrading stage 308, the first byproduct including at least one of non-oxidized hydrocarbon 3081 and/or diluent, such as oxygenate 3082; a conduit 3083 for conducting heteroatom species, such as $NO_R$, $SO_x$, $CO_2$, $N_2$, sulfuric acid, etc., away from upgrading stage 308; one or more conduits for conducting a second byproduct away from stage 208, the second byproduct including, e.g., one or more of molecular hydrogen 2082 or light saturated hydrocarbon 2083; one or more conduits for conducting away non-volatiles 2084 and/or heteroatom species, such as hydrogen sulfide 2085 away from upgrading stage 208; or one or more conduits (not shown) for adding to the second mixture one or more of (i) hydrogen; (ii) methane, ethane, and/or other light saturated hydrocarbon, or (iii) ethylene. Optionally, stages 208 and 308 can be utilized to provide streams for adjusting the composition of the first-fifth mixtures.

For example, when it is desired to (a) increase the relative amount of one or more of hydrocarbon (e.g., methane) and/or hydrogen in the fuel over that of its source material or (b) increase the relative amount of oxidant (e.g., oxygen and/or ozone) in the oxidant over that of its source material, this can be done as follows: (a) hydrocarbon, such as light saturated hydrocarbon, e.g., methane, can be added via conduit 3001. These species can be obtained from (i) external sources and/or (ii) sources within the process, such as from conduits 3081 or 2083, e.g., when optional stages 308 and 208 are utilized; and (b) oxidant is can be added via conduit 3003. The added oxidant can be obtained from (i) external sources and/or (ii) sources within the process such as from conduit 3082, e.g., when optional stage 308 is utilized and the oxygenate in conduit 3082 comprises oxidant. When the source material is air, the air can be obtained from a blower or compressor, for example.

When it is desired to increase the amount of one or more of molecular hydrogen, hydrocarbon (e.g., light saturated hydrocarbon, such as methane), and diluent in the first mixture, these can be added (e.g., in stage 204) as follows: (i) molecular hydrogen can be added via conduit 2043, with the added hydrogen obtained, e.g., from one or more of (a) from the process via conduit 2082 when optional stage 208 is present, (b) from molecular hydrogen separated from the first product, or (c) from an external source; (ii) hydrocarbon can be added via conduit 2044, which these species can be obtained from the process via conduit 3081 or 2083, e.g., when optional stages 308 and 208 are utilized, from hydrocarbon separated from the first product, or from an external source; and/or (iii) diluent (such as oxygenate) can be added via conduit 2045. The diluent can be obtained, e.g., (a) from the process via conduit 3082, when optional stage 308 is utilized, (b) from the first product, (c) from the second mixture, and/or (d) from a source external to the process.

While the present invention has been described and illustrated with respect to certain embodiments, it is to be understood that the invention is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed.

What is claimed is:

1. A hydrocarbon conversion method comprising:
    (a) introducing a first mixture comprising hydrocarbons to a regenerative reactor,
    (b) flowing the first mixture through a channeled reactor bed, the channeled reactor bed being located within the regenerative reactor, wherein
        (i) the channeled reactor bed includes first and second portions, the second portion being located downstream of the first portion with respect to the flow of first mixture;
        (ii) the first portion has a temperature in the range of about 325° C. to about 1125° C., a first plurality of flow passages for conducting the first mixture through the first portion, and a first wetted area $a_{v1}$;
        (iii) the second portion has a temperature in the range of about 1250° C. to 1615° C., a second plurality of flow passages for conducting the first mixture through the second portion, and a second wetted area $a_{v2}$; and
        (iv) the ratio of the second wetted area $a_{v2}$ to the first wetted area $a_{v1}$ is ≤0.75;
    (c) heating the first mixture in the first portion by transferring heat to the first mixture from the first portion at a first heat transfer rate to produce a heated first mixture; and
    (d) further heating the heated first mixture in the second portion by transferring heat to the heated first mixture from the second portion at a second heat transfer rate to react at least a portion of the heated first mixture's hydrocarbons within the second portion to produce a second mixture comprising $C_2$ unsaturates, wherein the flow of first mixture across the channeled reactor bed has a pressure drop that is less than that of a substantially similar comparative first mixture flow through a substantially similar comparative channeled reactor bed having a ratio $a_{v2}$ to $a_{v1}$ >0.75.

2. The method of claim 1, wherein the ratio of the second wetted area $a_{v2}$ to the first wetted area $a_{v1}$ of the channeled reactor bed is ≤0.5.

3. The method of claim 1, wherein the ratio of the second wetted area $a_{v2}$ to the first wetted area $a_{v1}$ of the channeled reactor bed is in the range of 0.05 to 0.75.

4. The method of claim 1, wherein the ratio of the second wetted area $a_{v2}$ to the first wetted area $a_{v1}$ of the channeled reactor bed is in the range of 0.1 to 0.5.

5. The method of claim 1, further comprising:
    (e) stop introducing the first mixture through the regenerative reactor and introducing a flow of fuel and a flow of oxidant through the regenerative reactor;
    (f) exothermically reacting the fuel and the oxidant in the regenerative reactor to produce heat and combustion products;
    (g) transferring heat from the combustion products to one or more of a first bed packing in the first portion forming the first plurality of flow passages and a second bed packing in the second portion forming the second plurality of flow passages; and
    (h) discontinuing the flow of the fuel, discontinuing the flow of the oxidant, removing the combustion products from the regenerative reactor, and re-introducing a flow of the first mixture into the regenerative reactor.

6. The method of claim 1, wherein the regenerative reactor further comprises a mixing zone.

7. The method of claim 6, wherein the mixing zone is disposed adjacent to the second portion.

8. The method of claim 1, wherein the regenerative reactor further comprises a mixing zone that consists essentially of a gap adjacent to the second portion.

9. The method of claim 1, wherein the channeled reactor bed has a third portion having a third plurality of flow passages with a third wetted area $a_{v3}$, wherein the ratio of the third wetted area $a_{v3}$ to the second wetted area $a_{v2}$ is ≤0.75; and further comprising passing at least one of the first mixture and the second mixture through the third portion.

10. The method of claim 1, wherein the channeled reactor bed has a third portion having a third plurality of flow passages with a third wetted area $a_{v3}$, and has a fourth portion having a fourth plurality of flow passages with a fourth wetted area $a_{v4}$, wherein the ratio of the third wetted area $a_{v3}$ to the fourth wetted area $a_{v4}$ is ≤0.75; and further comprising passing at least one of the first mixture and the second mixture through the third portion and the fourth portion.

11. The method of claim 1, wherein the channeled reactor bed has a third portion having a third plurality of flow passages with a third wetted area $a_{v3}$, and has a fourth portion having a fourth plurality of flow passages with a fourth wetted area $a_{a4}$, wherein the ratio of the third wetted area $a_{v3}$ to the fourth wetted area $a_{v4}$ is ≤0.75 and the ratio of the third wetted area $a_{v3}$ to the second wetted area $a_{v2}$ is in the range of 0.8 to 1.2; and further comprising passing at least one of the first mixture and the second mixture through the third portion and the fourth portion.

12. A hydrocarbon conversion method comprising:
   (a) introducing a first mixture comprising hydrocarbons to a regenerative reactor,
   (b) flowing the first mixture through first and second channeled reactor beds, the first and second channeled reactor beds being located within the regenerative reactor, wherein
      (i) the first channeled reactor bed includes first and second portions,
      (ii) the first portion has a temperature in the range of about 300° C. to about 1000° C., a plurality of flow passages for conducting the first mixture through the first portion, and a wetted area $a_{v1}$,
      (iii) the second portion has a temperature in the range of about 1200° C. to about 1800° C., a plurality of flow passages for conducting the first mixture through the second portion, and a second wetted area $a_{v2}$,
      (iv) the second wetted area $a_{v2}$ is substantially equal to $R_{21}$ times the first wetted area $a_{v1}$, with $R_{21}$ being ≤0.75, and
      (v) the first portion is located upstream of the second portion with respect to the flow of the first mixture; and
   (c) heating the first mixture in the first portion by transferring heat to the first mixture from the first portion at a first heat transfer rate to produce a heated first mixture; and
   (d) further heating the heated first mixture in the second portion by transferring heat to the heated first mixture from the second portion at a second heat transfer rate to react at least a portion of the heated first mixture's hydrocarbons within the second portion to produce a second mixture comprising $C_2$ unsaturates, wherein the flow of first mixture across the first channeled reactor bed has a pressure drop that is less than that of a substantially similar comparative first mixture flow through a substantially similar comparative first channeled reactor bed having an $R_{21}$>0.75.

13. The method of claim 12, wherein the first portion has a wetted area in the range of 330 m$^{-1}$ to 6500 m$^{-1}$.

14. The method of claim 12, wherein $R_{21}$ of the first channeled reactor bed is in the range of 0.05 to 0.75.

15. The method of claim 12, wherein $R_{21}$ of the first channeled reactor bed is in the range of 0.1 to 0.5.

16. The method of claim 12, further comprising:
   (e) stop introducing the first mixture through the regenerative reactor and introducing a flow of fuel and a flow of oxidant through the regenerative reactor, wherein the second channeled reactor bed is upstream of the first channeled reactor bed with respect to the flow of fuel and the flow of oxidant;
   (f) exothermically reacting the fuel and the oxidant in the regenerative reactor to produce heat and combustion products;
   (g) transferring heat from the combustion products to one or more of a first bed packing in the first portion forming the first plurality of flow passages and a second bed packing in the second portion forming the second plurality of flow passages; and
   (h) discontinuing the flow of the fuel, discontinuing the flow of the oxidant, removing the combustion products from the regenerative reactor, and re-introducing a flow of the first mixture into the regenerative reactor.

17. The method of claim 16, further comprising a mixing zone located between the first and second channeled reactor beds for mixing the flow of fuel with the flow of oxidant upstream of the first channeled reactor bed.

18. The method of claim 12, wherein
   (i) the first channeled reactor bed further comprises a third portion having a third plurality of flow passages with a third wetted area $a_{v3}$,
   (ii) $a_{v3}$ is substantially equal to $R_{32}$ times $a_{v2}$, with $R_{32}$ being ≤0.75; and
   (iii) at least a portion of the first mixture and/or at least a portion of the second mixture pass through the third portion.

19. The method of claim 12, wherein
   (i) the first channeled reactor bed further comprises third and fourth portions,
   (ii) the third portion has a third plurality of flow passages with a third wetted area $a_{v3}$,
   (iii) the fourth portion has a fourth plurality of flow passages with a fourth wetted area $a_{v4}$,
   (iv) $a_{v4}$ is substantially equal to $R_{43}$ times $a_{v3}$, with $R_{43}$ being ≤0.75,
   (v) $a_{v3}$ is substantially equal to $R_{32}$ times $a_{v2}$, with $R_{32}$ being ≤0.75, and
   (vi) at least a portion of the first mixture and/or at least a portion of the second mixture pass through the third portion and the fourth portion.

* * * * *